US012662456B2

(12) United States Patent
Mickle et al.

(10) Patent No.: US 12,662,456 B2
(45) Date of Patent: Jun. 23, 2026

(54) DEXTRORPHAN PRODRUGS AND PROCESSES FOR MAKING AND USING THEM

(71) Applicant: ZEVRA THERAPEUTICS, INC., Celebration, FL (US)

(72) Inventors: Travis Mickle, Celebration, FL (US); Sven Guenther, Coralville, IA (US); Sanjib Bera, Blacksburg, VA (US)

(73) Assignee: Zevra Therapeutics, Inc., Celebration, FL (US)

( * ) Notice: Subject to any disclaimer, the term of this patent is extended or adjusted under 35 U.S.C. 154(b) by 0 days.

(21) Appl. No.: 18/655,883

(22) Filed: May 6, 2024

(65) Prior Publication Data

US 2024/0317688 A1 Sep. 26, 2024

Related U.S. Application Data

(60) Division of application No. 17/537,291, filed on Nov. 29, 2021, now Pat. No. 12,012,384, which is a continuation of application No. 16/604,755, filed as application No. PCT/US2018/027266 on Apr. 12, 2018, now Pat. No. 11,214,544.

(60) Provisional application No. 62/485,894, filed on Apr. 14, 2017.

(51) Int. Cl.

| | |
|---|---|
| ***C07D 221/28*** | (2006.01) |
| ***A61K 31/439*** | (2006.01) |
| ***A61K 47/54*** | (2017.01) |

(52) U.S. Cl.

CPC .......... *C07D 221/28* (2013.01); *A61K 47/542* (2017.08)

(58) Field of Classification Search

CPC ...... A61K 31/439; C07D 221/28; A61P 25/04

USPC ............................................ 514/289; 546/74

See application file for complete search history.

(56) References Cited

U.S. PATENT DOCUMENTS

| | | | |
|---|---|---|---|
| 3,766,188 | A | 10/1973 | Murakami et al. |
| 4,673,679 | A | 6/1987 | Aungst et al. |
| 5,013,554 | A | 5/1991 | Passarolli et al. |
| 5,840,731 | A | 11/1998 | Mayer et al. |
| 5,932,589 | A | 8/1999 | Galliangeli et al. |
| 8,829,020 | B2 | 9/2014 | Cantrell et al. |
| 11,214,544 | B2 | 1/2022 | Mickle et al. |
| 11,234,975 | B2 | 2/2022 | Mickle et al. |
| 12,012,384 | B2 | 6/2024 | Mickle et al. |
| 2009/0312361 | A1 | 12/2009 | Streeper et al. |
| 2010/0286186 | A1 | 11/2010 | Franklin et al. |
| 2011/0002990 | A1 | 1/2011 | Mickle et al. |
| 2011/0105381 | A2 | 5/2011 | Jenkins et al. |
| 2011/0178068 | A1 | 7/2011 | Almarsson et al. |
| 2011/0245288 | A1 | 10/2011 | Stinchcomb et al. |

OTHER PUBLICATIONS

Compound with RN 139441-86-4 enterd in STN in 1992.
Fleishmann et al.: Effects of non-competitive NMDA receptor antagonists on reproductive and motor behaviors in female rats. Brain Res., vol. 568, pp. 138-146, 1991.
Koppel, C. et al.: Urinary metabolism og dextromethorphan in man. Arzneimittel-Forschung, vol. 37, pp. 1304-1306, 1987.
Compound with RN 917394-04-8 entered STN on Jan. 12, 2007.
International Bureau of WIPO, Transmittal of International Preliminary Report on Patentability regarding I\pplication No. PCT/US2018/027266, 18 pages, mailed Oct. 24, 2019.
Intemational Search Report for PCT Patent Application No. PCT/US2018/027266 dated Aug. 9, 2018.
Eldridge, JA, "Synthesis and Stability Studies of Prodrugs and Codrugs of Naltrexone and 6-Beta-Naltrexol", Doctoral Thesis, University of Kentucky, pp. 1-126; 2013, p. 1, paragraph 1; p. 7, paragraph 1, p. 18, paragraph 1; p. 123, see structure.

*Primary Examiner* — Charanjit Aulakh
(74) *Attorney, Agent, or Firm* — Taft Stettinius & Hollister LLP

(57) ABSTRACT

The presently described technology provides compositions of one or more of oxoacids, polyethylene glycols, and vitamin compounds chemically conjugated to dextrorphan, (+)-17-methylmorphinan-3-ol), to form novel prodrugs and compositions of levorphanol.

16 Claims, 20 Drawing Sheets

FIGURE 1
STRUCTURES OF SOME HYDROXYBENZOATES

benzoic acid

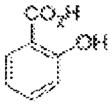
salicylic acid

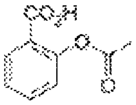
aspirin

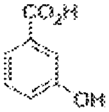
3-hydroxy-benzoic acid

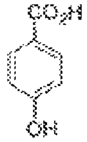
4-hydroxy-benzoic acid

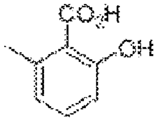
6-methylsalicylic acid

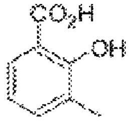
o-cresotinic acid

R = aliphatic chain

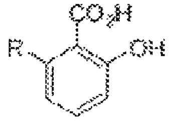
anacardic acids

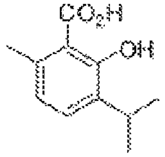
o-thymotic acid

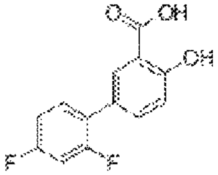
diflunisal

p-anisic acid

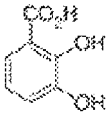
2,3-dihydroxy-benzoic acid (2,3-DHB)

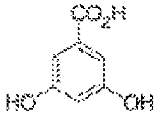
α-resorcylic acid

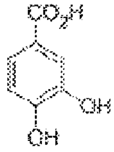
protocatechuic acid

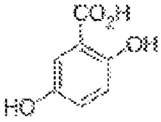
gentisic acid

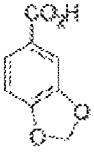
piperonylic acid

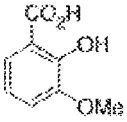
3-methoxy-salicylic acid

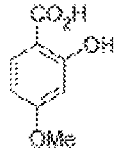
4-methoxy-salicylic acid

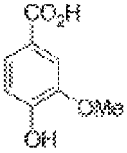
vanillic acid

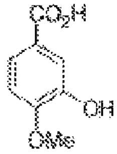
isovanillic acid

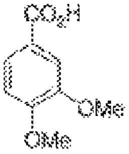
veratric acid

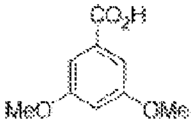
3,5-dimethoxy-benzoic acid

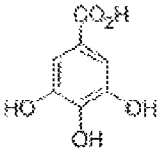
gallic acid

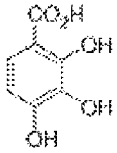
2,3,4-trihydroxy-benzoic acid

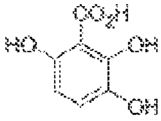
2,3,6-trihydroxy-benzoic acid

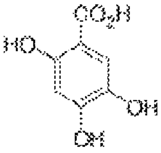
2,4,5-trihydroxy-benzoic acid

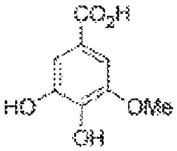
3-O-methylgallic acid (3-OMGA)

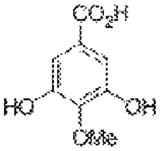
4-O-methylgallic acid (4-OMGA)

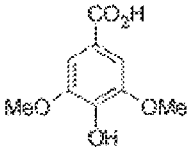
syringic acid

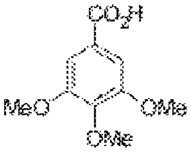
3,4,5-trimethoxy-benzoic acid

FIGURE 2
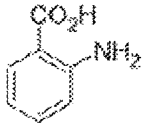
anthranilic acid
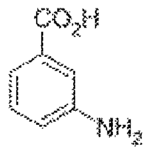
3-aminobenzoic acid
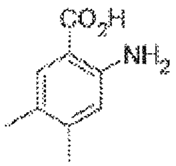
4,5-dimethyl-
anthranilic acid
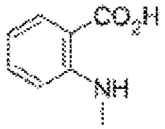
*N*-methylanthranilic acid
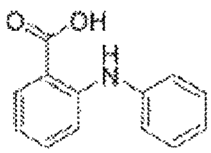
fenamic acid
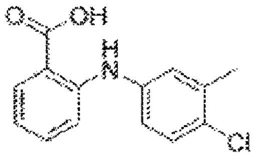
tolfenamic acid
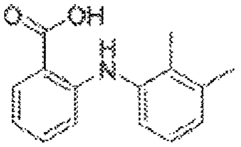
mefenamic acid
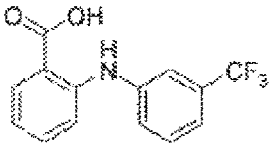
flufenamic acid
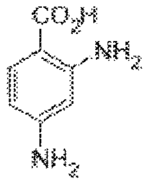
2,4-diaminobenzoic acid
(2,4-DABA)
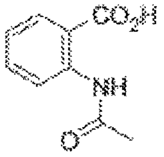
*N*-acetylanthranilic acid
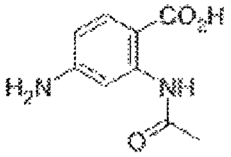
2-acetylamino-
4-aminobenzoic acid
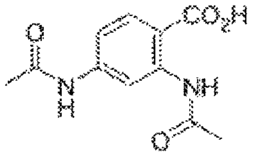
2,4-diacetylamino-
benzoic acid FIGURE 3
STRUCTURES OF SOME HETEROARYL CARBOXYLIC ACIDS
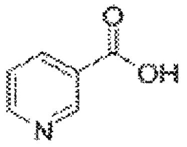
nicotinic acid
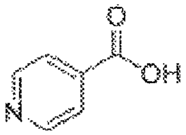
isonicotinic acid
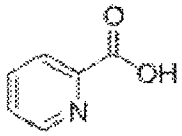
picolinic acid
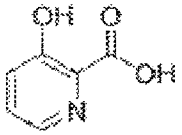
3-hydroxypicolinic acid
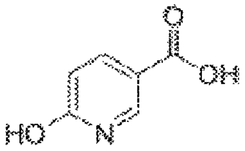
6-hydroxynicotinic acid
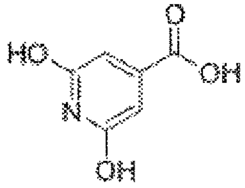
citrazinic acid
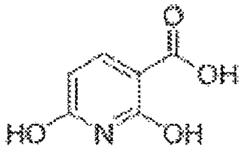
2,6-dihydroxynicotinic acid
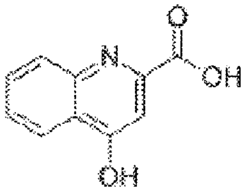
kynurenic acid
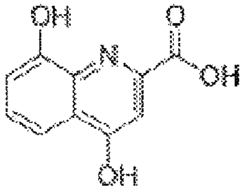
xanthurenic acid
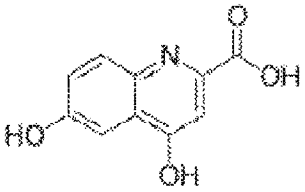
6-hydroxy-
kynurenic acid
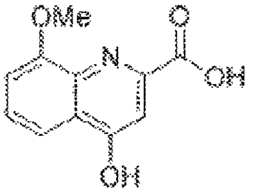
8-methoxykynurenic acid
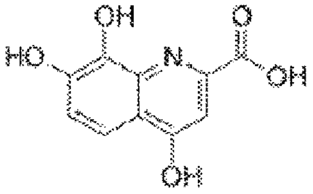
7,8-dihydroxy-
kynurenic acid
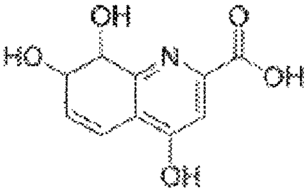
7,8-dihydro-7,8-di-
hydroxykynurenic acid

FIGURE 4

STRUCTURES OF SOME PHENYLACETATES

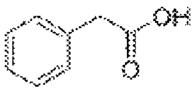
phenylacetic acid (hydratropic acid)

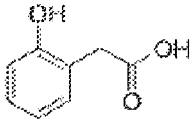
2-hydroxyphenyl-acetic acid

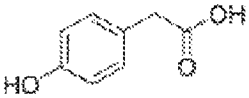
4-hydroxyphenyl-acetic acid

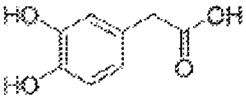
homoprotocatechuic acid

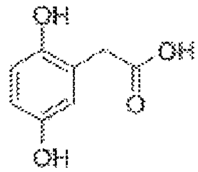
homogentisic acid

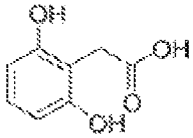
2,6-dihydroxy-phenylacetic acid

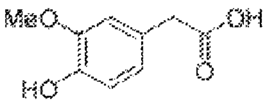
homovanillic acid

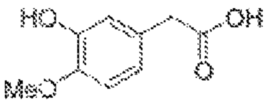
homoisovanillic acid

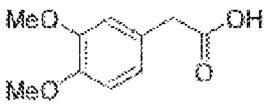
homoveratric acid

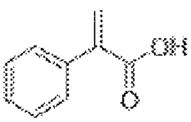
atropic acid

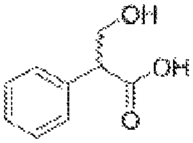
tropic acid

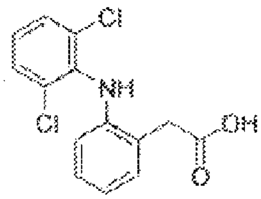
diclofenac

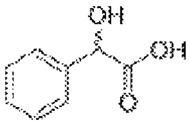
mandelic acid

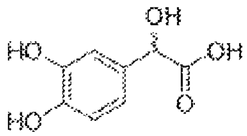
3,4-dihydroxymandelic acid

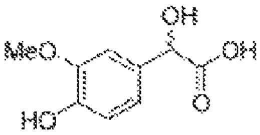
vanillylmandelic acid

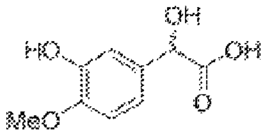
isovanillylmandelic acid

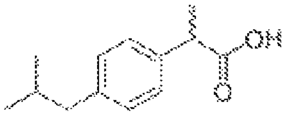
ibuprofen

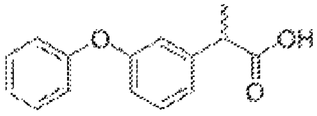
fenoprofen

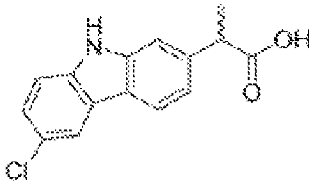
carprofen

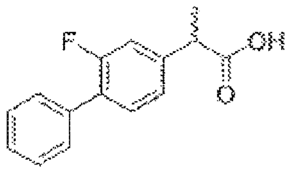
flurbiprofen

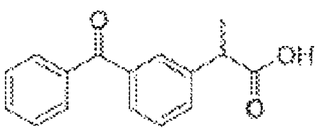
ketoprofen

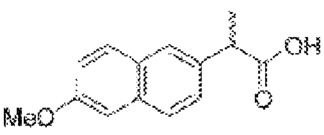
naproxen

FIGURE 5
STRUCTURES OF SOME BENZYLACETATES
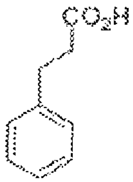
3-phenylpropanoic acid
(benzylacetic acid)
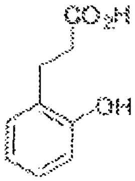
Melilotic acid
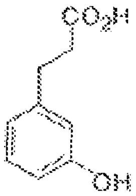
3-hydroxyphenyl-
propanoic acid
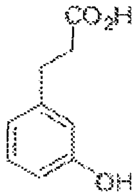
4-hydroxyphenyl-
propanoic acid
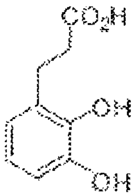
2,3-dihydroxyphenyl-
propanoic acid
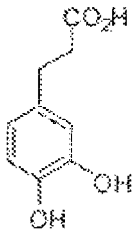
3,4-dihydroxyphenyl-
propanoic acid
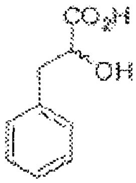
Phenyllactic acid FIGURE 6
STRUCTURES OF SOME CINNAMATES
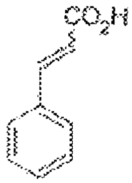
cinnamic acid
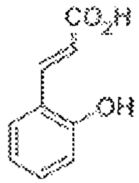
*o*-coumaric acid
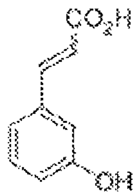
*m*-coumaric acid
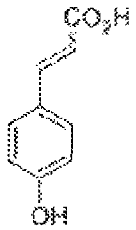
*p*-coumaric acid
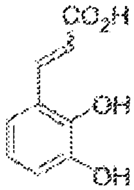
2,3-dihydroxy-cinnamic acid
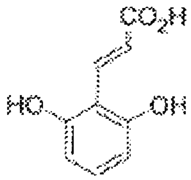
2,6-dihydroxy-cinnamic acid
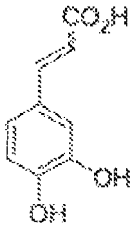
caffeic acid
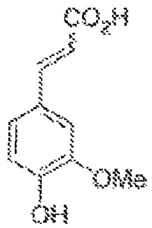
ferulic acid
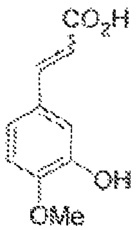
isoferulic acid
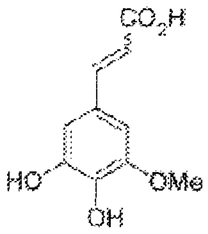
5-hydroxyferulic acid
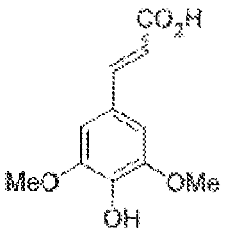
sinapic acid
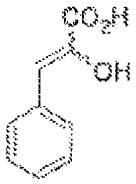
2-hydroxy-3-phenyl-propenoic acid

FIGURE 7

STRUCTURES OF SOME DICARBOXYLIC ACIDS

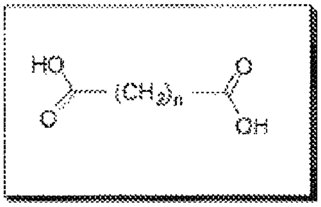

When n = 0 Oxalic acid
n = 1 Malonic acid
n = 2 Succinic acid
n= 3 Glutraic acid
n= 4 Adipic acid
n= 5 Pimelic acid
n = 6 Suberic acid
n = 7 Azelaic acid
n = 8 Sebacic acid

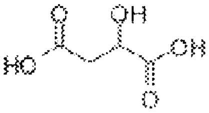

Malic acid

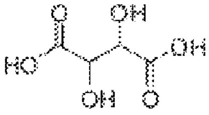

Tartaric acid

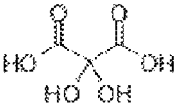

dihydroxymesoxalic acid

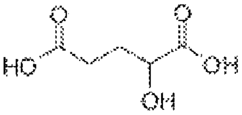

α-hydroxyglutaric acid

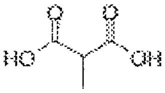

Methylmalonic acid

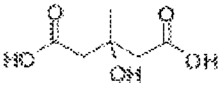

Meglutol

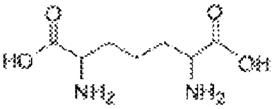

Diaminopimelic acid

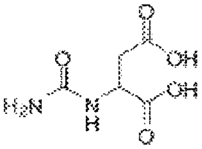

Carbamoyl aspartic acid

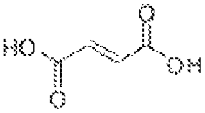

Fumaric acid (trans isomer)
Maleic acid (cis isomer)

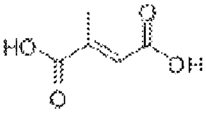

Mesaconic acid

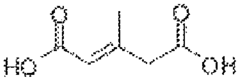

3-methylglutaconic acid

Traumatic acid

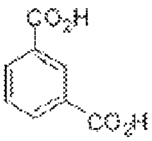

isophthalic acid

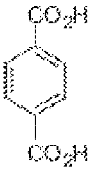

Terephthalic acid

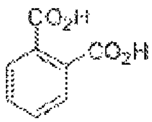

Phthalic acid

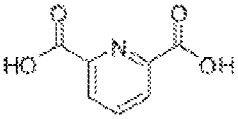

Dipicolinic acid

FIGURE 8
STRUCTURES OF SOME TRICARBOXYLIC ACIDS
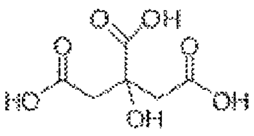
Citric acid
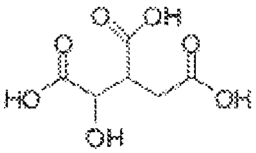
Isocitric acid
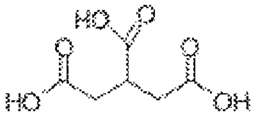
Carballylic acid
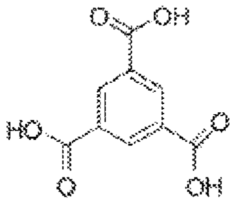
Trimesic acid FIGURE 9
GENERAL STRUCTURES OF THE STANDARD AMINO ACIDS
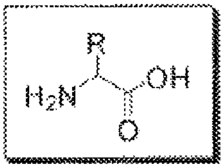
R =
-H Glycine
$-CH_3$ Alanine
 Phenylalanine
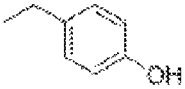 Tyrosine
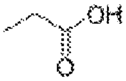 Aspartic acid
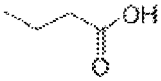 Glutamic acid
 Asparagine
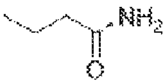 Glutamine
 Lysine
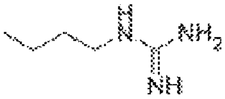 Arginine
 Selenocysteine
 Histidine
 Serine
 Cysteine
 Threonine
 Methionine
 Valine
 Leucine
 Isoleucine
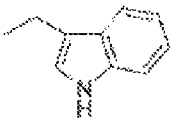 Tryptophan
 Proline
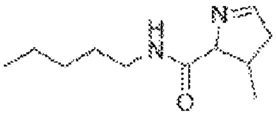 Pyrrolysine FIGURE 10
STRUCTURES OF SOME NON-STANDARD AMINO ACIDS
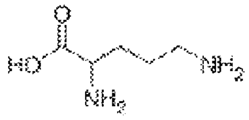
Ornithine
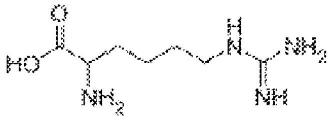
Homoarginine
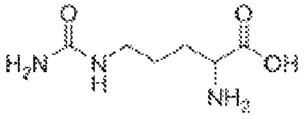
Citrulline
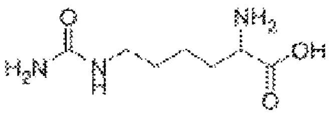
Homocitrulline
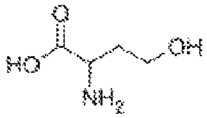
Homoserine
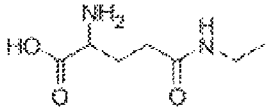
Theanine
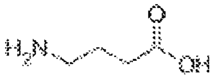
γ-Aminobutyric acid
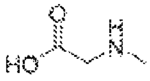
Sarcosine
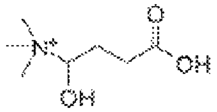
Carnitine
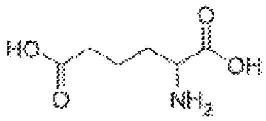
2-Aminoadipic acid
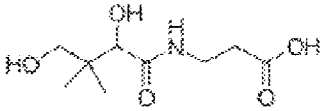
Pantothenic acid
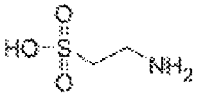
Taurine
Hypotaurine
Lanthionine
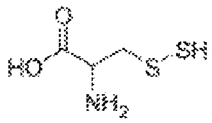
Thiocysteine
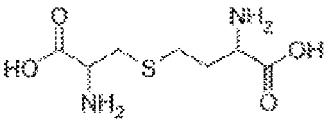
Cystathionine
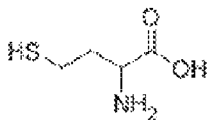
Homocysteine FIGURE 10 (CONT.)
β-Alanine
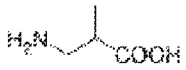
β-Aminoisobutyric acid
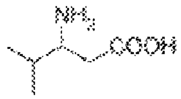
β-Leucine
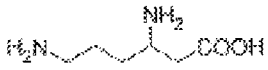
β-Lysine
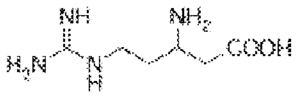
β-Arginine
β-Glutamate
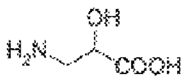
Isoserine
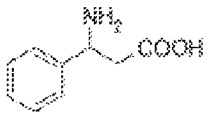
β-Phenylalanine
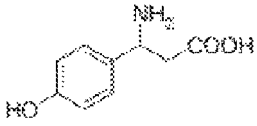
β-Tyrosine
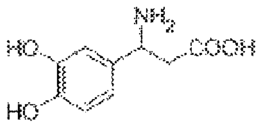
β-Dopa
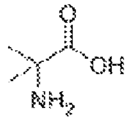
2-Aminoisobutyric acid
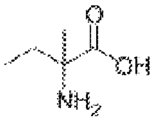
Isovaline
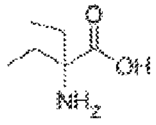
Di-n-ethylglycine
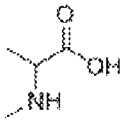
*N*-Methyl-alanine
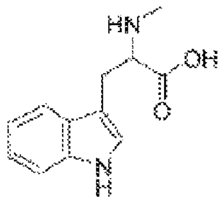
L-Abrine FIGURE 10 (CONT.)
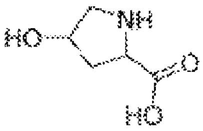
4-Hydroxyproline
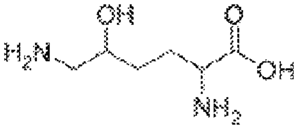
5-Hydroxylysine
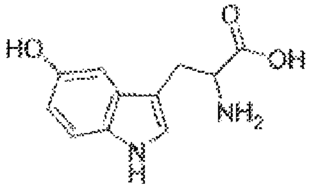
5-Hydroxy-tryptophan
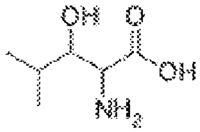
3-Hydroxyleucine
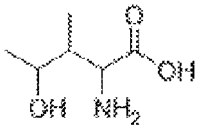
4-Hydroxyisoleucine
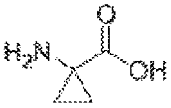
1-Aminocyclopropyl-1-carboxylic acid
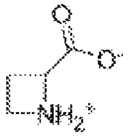
Azetidine-2-carboxylic acid
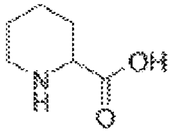
Pipecolic acid

FIGURE 11

STRUCTURES OF SOME SYNTHETIC AMINO ACIDS

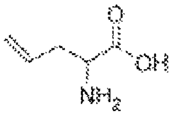
Allylglycine

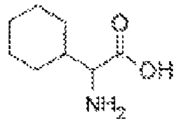
Cyclohexylglycine

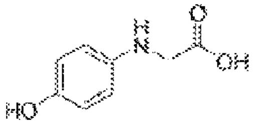
*N*-(4-Hydroxyphenyl)glycine

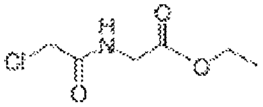
*N*-(Chloroacetyl)glycine ethyl ester

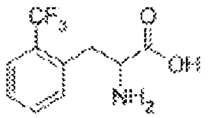
2-(Trifluoromethyl)-phenylalanine

4-(Hydroxymethyl)-phenylalanine

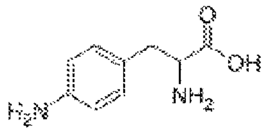
4-Amino-phenylalanine

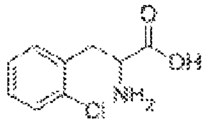
2-Chlorophenylglycine

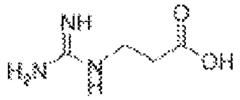
3-Guanidinopropionic acid

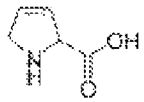
3,4-Dehydro-proline

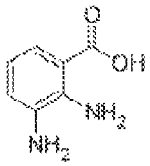
2,3-Diaminobenzoic acid

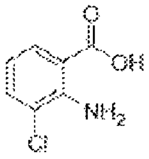
2-Amino-3-chlorobenzoic acid

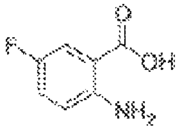
2-Amino-5-fluorobenzoic acid

FIGURE 12A
CHEMICAL STRUCTURES OF WATER SOLUBLE VITAMINS
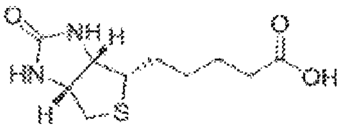
Biotin (Vitamin $B_7$)
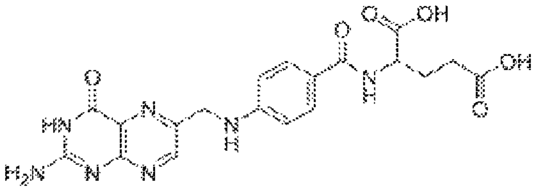
Folic Acid
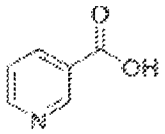
Niacin
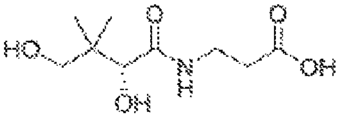
Pantothenic acid (Vitamin $B_5$)
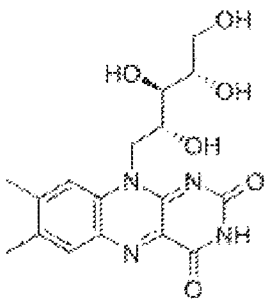
Riboflavin (Vitamin $B_2$)
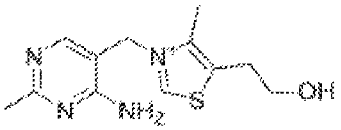
Thiamin (Vitamin $B_1$)
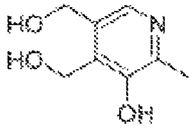
Pyridoxine (Vitamin $B_6$)
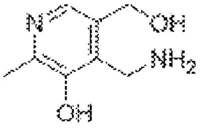
Pyridoxamine (Vitamin $B_6$)
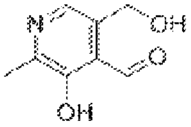
Pyridoxal (Vitamin $B_6$)
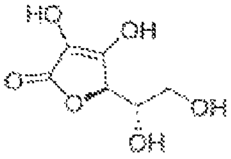
Ascorbic acid (Vitamin C)

FIGURE 12B
CHEMICAL STRUCTURES OF FAT SOLUBLE VITAMINS
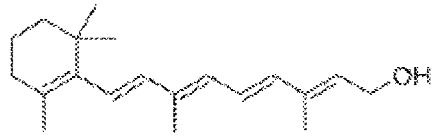
Retinol (Vitamin A)
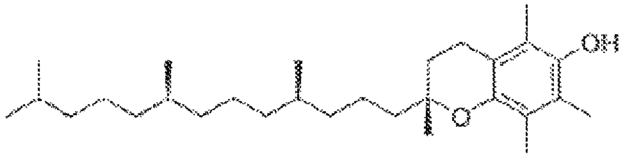
Alpha-tocopherol (Vitamin E)
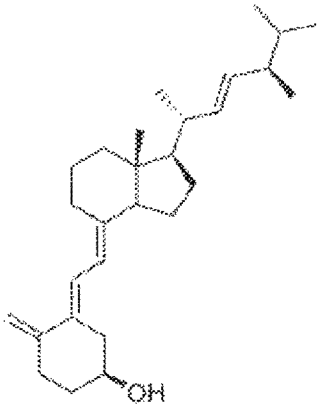
Calciferol (Vitamin $D_2$)
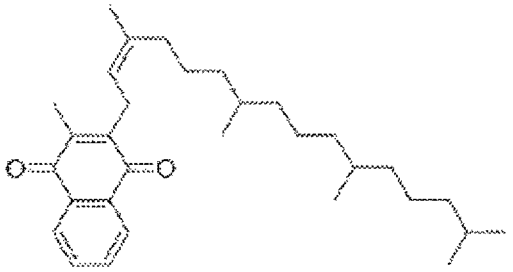
Phylloquinone (Vitamin $K_1$)
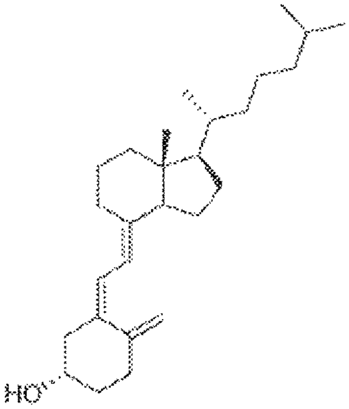
Cholecalciferol (Vitamin $D_3$)

DEXTRORPHAN PRODRUGS AND PROCESSES FOR MAKING AND USING THEM

CROSS REFERENCE TO RELATED APPLICATIONS

This application is a divisional of U.S. patent application Ser. No. 17/537,291, filed Nov. 29, 2021, which is a continuation of U.S. patent application Ser. No. 16/604,755, filed Oct. 11, 2019, which claims priority to International Patent Application No. PCT/US2018/027266, filed Apr. 12, 2018, which claims priority to U.S. provisional application No. 62/485,894, filed Apr. 14, 2017, all of which are herein incorporated by reference in their entirety. This application is also related to U.S. provisional application No. 62/485,888, filed Apr. 14, 2017; U.S. provisional application No. 62/485,890, filed Apr. 14, 2017; and U.S. provisional application No. 62/485,891, filed Apr. 14, 2017.

BACKGROUND OF THE INVENTION

Opioids are highly effective as analgesics and are commonly prescribed for the treatment of acute and chronic pain. They are also commonly used as antitussives. The opioids, however, also produce euphoria and are highly addictive. As a result they are often abused with far reaching social and health related consequences.

Because of the inherent potential for abuse, it is desirable that any pharmaceutical composition containing an opioid agonist be made as abuse-resistant or abuse-deterrent as practical. Illicit users often will attempt to circumvent the extended release properties of these dosage forms by injecting or otherwise misusing the product in order to achieve an immediate release of the opioid agonist.

Dextrorphan ((+)-17-methylmorphinan-3-ol) is the (+)-isomer and one of two enantiomers of 17-methylmorphinan-3-ol. The other enantiomer is levorphanol ((−)-17-methylmorphinan-3-ol). A 1:1 mixture of both enantiomers (dextrorphan and levorphanol) is referred to as racemorphan.

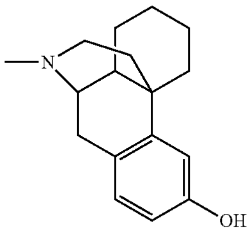

17-Methylmorphinan-3-ol

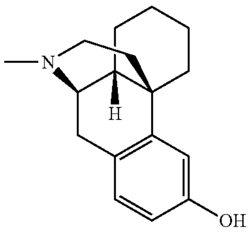

Levorphanol

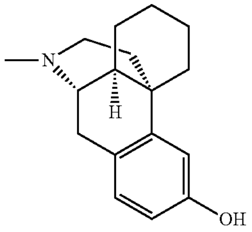

Dextrorphan

It should be appreciated by those skilled in the art that different stereochemistry may impact the pharmacodynamics, pharmacological and/or pharmacokinetic properties, among other properties, of each isomer or racemic mixture utilized. Further, it should also be appreciated that various conjugations of the isomers to various ligands may also impact the pharmacodynamics, pharmacological and/or pharmacokinetic properties, among other properties, of each resultant conjugate, formulation, and/or end product. For example, those skilled in the art can appreciate the pharmacodynamics, pharmacological and/or pharmacokinetic property differences exhibited and/or observed by different enantiomers (dextrorphan and levorphanol) as well as a mixture such as racemorphan. Moreover, those skilled in the art, also appreciate that the conjugation of those various different enantiomers may impact the various properties observed for the resultant dextrorphan or levorphanol conjugate, formulation and/or end product. Furthermore, those skilled in the art can recognize that conjugation to dextrorphan, levorphanol, or a mixture thereof, may create new enantiomers or diastereomers that may affect their resulting pharmacodynamic, pharmacological and/or pharmacokinetic properties.

Dextrorphan is a narcotic analgesic, which interacts predominantly with receptors in the central nervous system (CNS). It is also an active metabolite of dextromethorphan that forms after O-demethylation by CYP2D6. Dextrorphan has a wide range of pharmacological activities including weak μ-opioid agonism, (μ-opioid receptor (MOR)) and κ-opioid receptor agonism (KOR), as well as σ receptor agonism. Dextrorphan is also an NMDA (N-methyl-D-aspartate) receptor antagonist and a reuptake inhibitor of serotonin (SRI) and norepinephrine. In addition, dextrorphan is an antagonist of the $\alpha_3\beta_4$, $\alpha_4\beta_2$ and $\alpha_7$ nicotinic acetylcholine receptors, and the glycine receptor. Furthermore, dextrorphan blocks the L-Type voltage-gated calcium channel (LVGCC). This multimodal pharmacological profile may be effective for the treatment of CNS conditions including, but not limited to, pain, cough, neuropathic pain, cancer pain, opioid-induced hyperalgesia, pain syndromes that are refractory to other analgesic medications, post-therapeutic neuralgia, depression, narcolepsy and hyperalgesia.

The present technology utilizes covalent conjugation of the opioid dextrorphan with certain oxoacids, amino acids, polyethylene glycols (PEG or PEO), and vitamin compounds via an ester or carbonate linkage to decrease its potential for causing overdose or abuse by requiring the active dextrorphan to be released through enzymatic or metabolic breakdown of the conjugate in vivo. The present technology also provides methods of delivering dextrorphan as conjugates that release the dextrorphan following oral administration while being resistant to abuse by circuitous routes such as intravenous ("shooting") injection and intranasal administration ("snorting"). The compounds and conjugates of this disclosure (aka prodrugs) may be administered alone, or combined with other CNS agents, for the treatment of CNS conditions, including, but not limited to, pain, cough, neuropathic pain, cancer pain, opioid-induced hyperalgesia, pain syndromes that are refractory to other analgesic medications, post-therapeutic neuralgia, depression, narcolepsy and hyperalgesia.

BRIEF SUMMARY OF THE INVENTION

The present technology utilizes conjugation of the opioid dextrorphan with certain oxoacids, amino acids, polyethylene glycols (PEG or PEO), and/or vitamin compounds to decrease its potential for causing overdose or abuse by requiring the active dextrorphan to be released through enzymatic or metabolic breakdown of the conjugate in vivo.

The present technology also provides methods of delivering dextrorphan as conjugates that release the dextrorphan following oral administration while being resistant to abuse by circuitous routes such as intravenous ("shooting") injection and intranasal administration ("snorting").

Advantages of certain embodiments of the dextrorphan prodrugs of the present technology include, but are not limited to, reduced drug abuse potential, reduced or eliminated opioid induced constipation (OIC), reduced risk of chemical or physical manipulation resulting in full dosage of dextrorphan release, reduced patient to patient variability in plasma concentrations compared to free dextrorphan, improved dosage forms through modifications of the physical and chemical properties of the prodrugs.

In some aspects, the present technology provides an immediate release composition of conjugated dextrorphan that allows delivery of the dextrorphan into the blood system of a human or animal in a therapeutically bioequivalent manner upon oral administration. In at least one aspect, the compositions/formulations of the current technology can lessen common side effects associated with unconjugated dextrorphan and similar compounds. The presently described technology, in at least one aspect, provides a slow/sustained/controlled release composition of conjugated dextrorphan that allows slow/sustained/controlled delivery of the dextrorphan into the blood system of a human or animal within a safe therapeutic window upon, for example, oral administration.

In one aspect, the present technology provides a composition comprising at least one conjugate of dextrorphan, and at least one oxoacid, amino acid, polyethylene glycol, vitamin compound, or derivatives thereof. In some aspects, the conjugate further comprises a linker, wherein the linker chemically bonds the at least one dextrorphan with the at least one oxoacid, amino acid, polyethylene glycol, vitamin compound, or derivatives thereof.

In a further aspect, the present technology provides a composition comprising at least one conjugate of dextrorphan, wherein the conjugate has the following general Formula IA:

Formula IA

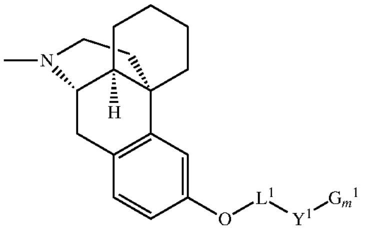

where $L^1$ is absent, or is

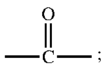

$Y^1$ is absent, or $[A\text{-}X—Z]_n$ where A, X, Z are independently absent or selected from —O—, —S— or $—(CR^1R^2)_k—$ $R^1$, $R^2$ are independently selected from H, alkyl, aryl, alkylaryl, alkoxy, haloalkyl, haloaryl n and k are independently 1-4

$G_m^1$ is absent or selected independently for each repeating subunit from H, amino acid, oxoacid, polyethylene glycol having from 2 to 5 ethylene oxide units, or a vitamin compound, and m is 1-4, except that m is 1 when $G^1$ is a hydrogen atom.

In a further aspect, the present technology provides a composition comprising at least one conjugate of dextrorphan, wherein the conjugate has the following general Formula IB:

Formula IB

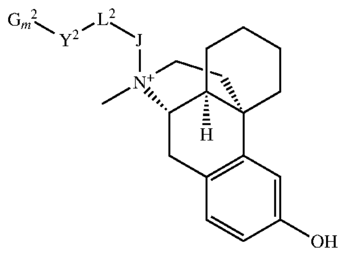

where $L^2$ is absent, or is

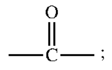

$Y^2$ is absent, or $[A\text{-}X—Z]_n$ where A, X, Z are independently absent or selected from —O—, —S— or $—(CR^1R^2)_k—$ J is $[M\text{-}W]_p$ where M is $—(CR^3R^4)_q—$; and W is absent, or —O— or —S—

$R^1$, $R^2$, $R^3$, $R^4$ are each independently selected from H, alkyl, aryl, alkylaryl, alkoxy, haloalkyl, haloaryl n and k are independently 1-4 p and q are independently 1-4

$G_m^2$ is absent or selected independently for each repeating subunit from H, amino acid, oxoacid, polyethylene glycol having from 2 to 5 ethylene oxide units, or a vitamin compound, and m is 1-4, except that m is 1 when $G^2$ is a hydrogen atom.

In a further aspect, the present technology provides a composition comprising at least one conjugate of dextrorphan, wherein the conjugate has the following general Formula IC:

Formula IC

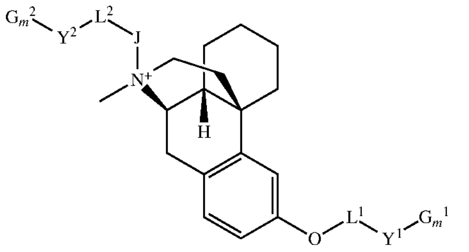

where $L^1$ and $L^2$ are independently absent, or is

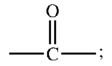

$Y^1$ and $Y^2$ are independently either absent, or $[A-X—Z]_n$ where A, X, Z are independently selected for $Y^1$ and $Y^2$, and are independent of each other either absent or selected from the group of —O—, —S—, or $—(CR^1R^2)_k—$ J is [M-W]p where M is $—(CR^3R^4)_q—$; and W is absent, or —O— or —S—

$R^1$, $R^2$, $R^3$, $R^4$ are each independently selected for $Y^1$ and $Y^2$, and are independent of each other selected from the group of H, alkyl, aryl, alkylaryl, alkoxy, haloalkyl, haloaryl For each $Y^1$ and $Y^2$, n is independently an integer of 1-4.

For each repeating unit of $[A-X—Z]_n$, k is independently an integer of 1-4.

p and q are independently 1-4

$G^1_m$ and $G^2_m$ are independently absent, or selected independently of each other and for each repeating subunit from H, amino acid, oxoacid, polyethylene glycol having from 2 to 5 ethylene oxide units, or a vitamin compound;

where m is selected independently for $G^1$ and $G^2$, and is an integer of 1-4, except that m is 1 when $G^1$ or $G^2$ is a hydrogen atom.

In another aspect, the present technology provides at least one prodrug composition comprising at least one conjugate, where dextrorphan is conjugated at the C-3 hydroxyl position, and wherein the at least one conjugate can be, for example, 3-Val-dextrorphan; 3-(PhePhePhe)-dextrorphan; 3-(ValValPhe)-dextrorphan; 3-(AlaAlaVal)-dextrorphan; 3-(GlyGlyAla)-dextrorphan; 3-hippuryl-dextrorphan; 3-(N-acetyl-Tyr)-dextrorphan; 3-(N-acetyl-Ile)-dextrorphan; 3-(ProProPhe)-dextrorphan; 3-(GlyGly)-dextrorphan; 3-(ValGly)-dextrorphan; 3-(AlaPro)-dextrorphan; 3-cinnamoyl-dextrorphan; 3-biotinyl-dextrorphan; 3-(N,O-diacetyl-Tyr)-dextrorphan; 3-(N-acetyl-Val-$OCH_2OC(O)$)-dextrorphan; 3-(cinnamoyl-$OCH_2OC(O)$)-dextrorphan; 3-(benzoyl-$OCH_2OC(O)$-dextrorphan; 3-(butanoyl-$OCH_2OC(O)$)-dextrorphan; 3-(N,O-acetyl-Lys-$OCH_2OC(O)$)-dextrorphan; 3-(acetyl-$OCH(CH_3)C(O)$)-dextrorphan; 3-(acetyl-$OCH_2C(O)$)-dextrorphan; 3-(acetyl-OCH(phenyl)C(O))-dextrorphan; 3-(methoxy-$PEG_2$-$CH_2C(O)$)-dextrorphan; 3-(methoxy-(ethoxy)-$CH_2C(O)$)-dextrorphan; 3-(N-succinoyl-Val)-dextrorphan; 3-($H_2N$-$PEG_4$-$CH_2CH_2C(O)$)-dextrorphan; 3-($N_3$-$PEG_4$-$CH_2CH_2C(O)$)-dextrorphan; 3-($H_2N$-$PEG_5$-$CH_2CH_2C(O)$)-dextrorphan, 3-(propyl-SC(O))-dextrorphan, 3-(ethoxy-C(O))-dextrorphan and anionic salts thereof, including hydrochloride/chloride salts.

In another aspect, the present technology provides at least one prodrug composition comprising at least one conjugate, where dextrorphan is conjugated at the N-17 position, and wherein the at least one conjugate can be, for example, N-(acetyl-$OCH_2$)-dextrorphanium; N-(pivaloyl-$OCH_2$)-dextrorphanium; N-(Ser-Ile-$CH_2$)-dextrorphanium; N-(Val-$CH_2$)-dextrorphanium; N-(Phe-Val-$CH_2$)-dextrorphanium; 3-(Phe-CH(Me)C(O))—N-(nicotinoyl-$OCH_2$)-dextrorphanium; N-(MeO-$PEG_3$-$CH_2C(O)OCH_2$)-dextrorphanium; N—(HO-$PEG_4$-$CH_2CH_2C(O)CH_2$)-dextrorphanium; N—(BzO-$CH_2OC(O)OCH_2$)-dextrorphanium; N-(Ala-$CH_2OC(O)OCH_2$)-dextrorphanium; N-(Pro-Val-$CH_2OC(O)OCH_2$)-dextrorphanium; N-(thiaminyl-$C(O)OCH_2$)-dextrorphanium; N-(cinnamoyl-$OCH_2SC(O)SCH_2$)-dextrorphanium; and anionic salts thereof, including hydrochloride/chloride salts.

In another aspect, the present technology provides at least one prodrug composition comprising at least one conjugate, where dextrorphan is conjugated at both the C-3 hydroxyl and the N-17 position, and wherein the at least one conjugate can be, for example, 3-acetyl-N-(acetyl-$OCH_2$)-dextrorphanium; 3-(pivaloyl)-N-(pivaloyl-$OCH_2$)-dextrorphanium; 3-(ethoxy-C(O))—N-(ethoxy-$C(O)CH(CH_3)$)-dextrorphanium; 3-(EtO—C(O))—N—($H_2N$-$PEG_2$-$CH_2CH_2C(O)OCH_2$)-dextrorphanium; 3-(Ac-Val)-N-(Phe-Phe-$CH_2$)-dextrorphanium; 3-(acetylsalicyloyl-$OCH_2OC(O)$)—N—(Ac-Val-$CH_2$)-dextrorphanium; 3-(Phe-CH(Me)C(O))—N-(nicotinoyl-$OCH_2$)-dextrorphanium, and anionic salts thereof, including hydrochloride/chloride salts.

In yet another aspect, the present technology provides a method for chemically synthesizing any of the dextrorphan conjugates of the present technology by performing the appropriate steps to conjugate dextrorphan to at least one ligand.

BRIEF DESCRIPTION OF THE DRAWINGS

FIG. 1. Chemical structures of some hydroxybenzoates for use in the making of the conjugates of the present technology.

FIG. 2. Chemical structures of some aminobenzoic acids for use in the making of the conjugates of the present technology.

FIG. 3. Chemical structures of some heteroaryl carboxylic acids for use in the making of the conjugates of the present technology.

FIG. 4. Chemical structures of some phenylacetates for use in the making of the conjugates of the present technology.

FIG. 5. Chemical structures of some benzylacetates for use in the making of the conjugates of the present technology.

FIG. 6. Chemical structures of some cinnamates for use in the making of the conjugates of the present technology.

FIG. 7. Chemical structures of some dicarboxylic acids for use in the making of the conjugates of the present technology.

FIG. 8. Chemical structures of some tricarboxylic acids for use in the making of the conjugates of the present technology.

FIG. 9. Chemical structures of some standard amino acids for use in the making of the conjugates of the present technology.

FIG. 10. Chemical structures of some non-standard amino acids for use in the making of the conjugates of the present technology.

FIG. 11. Chemical structures of some synthetic amino acids for use in the making of the conjugates of the present technology.

FIG. 12A. Chemical structures of some water soluble vitamins for use in the making of the conjugates of the present technology.

FIG. 12B. Chemical structures of some fat soluble vitamins for use in the making of the conjugates of the present technology.

DETAILED DESCRIPTION

Figure 13:
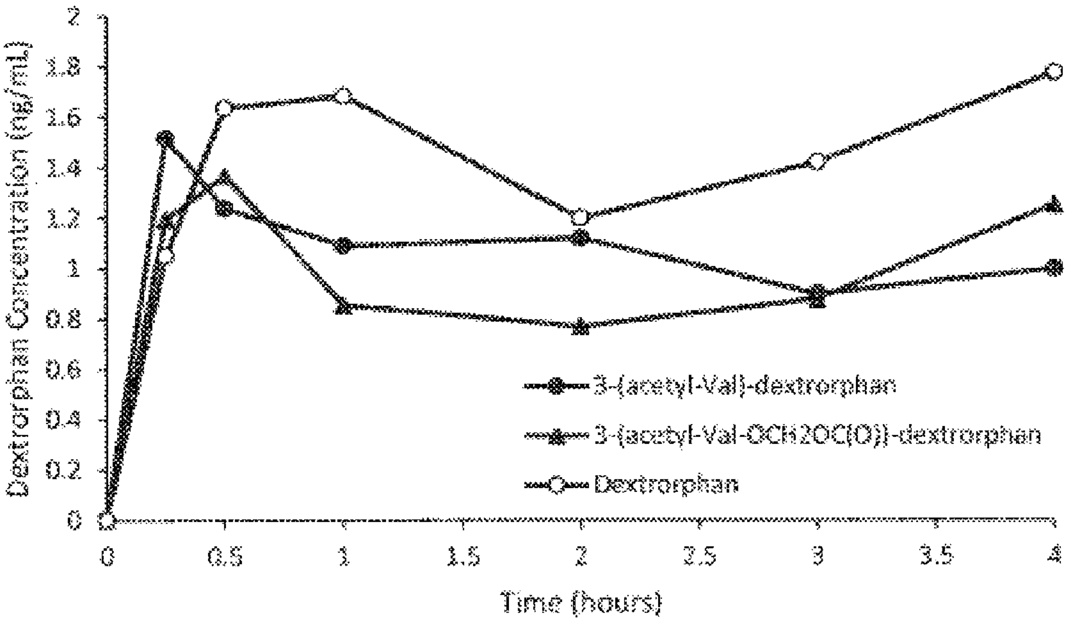
FIG. 13. Oral PK curves comparing 3-(N-acetyl-Val)-dextrorphan conjugate and 3-(N-acetyl-Val-OCH2OC (O))-dextrorphan conjugate with unconjugated dextrorphan in rats.
Figure 14:
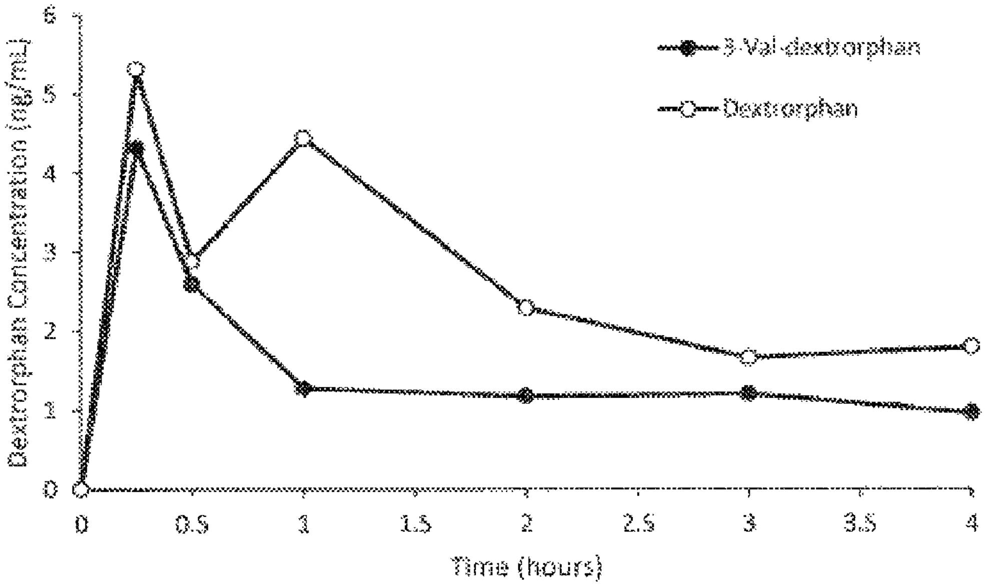
FIG. 14. Oral PK curves comparing 3-Val-dextrorphan conjugate with unconjugated dextrorphan in rats.
Figure 15:
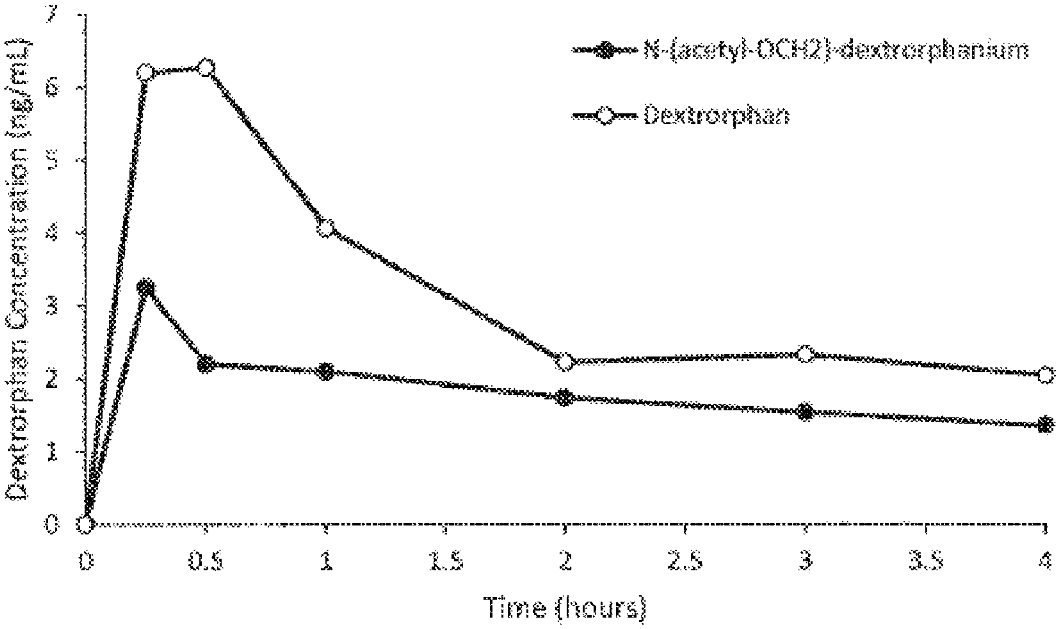
FIG. 15. Oral PK curves comparing N-(acetyl-$OCH_2$)-dextrorphanium conjugate with unconjugated dextrorphan in rats.
Figure 16:
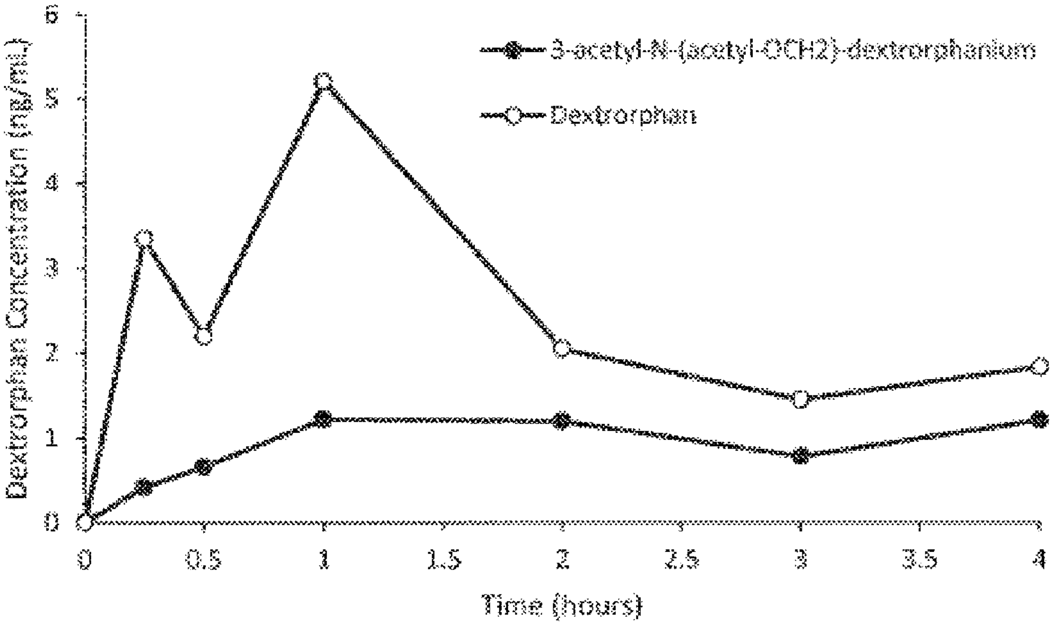
FIG. 16. Oral PK curves comparing 3-acetyl-N-(acetyl-$OCH_2$)-dextrorphanium conjugate with unconjugated dextrorphan in rats.
Figure 17:
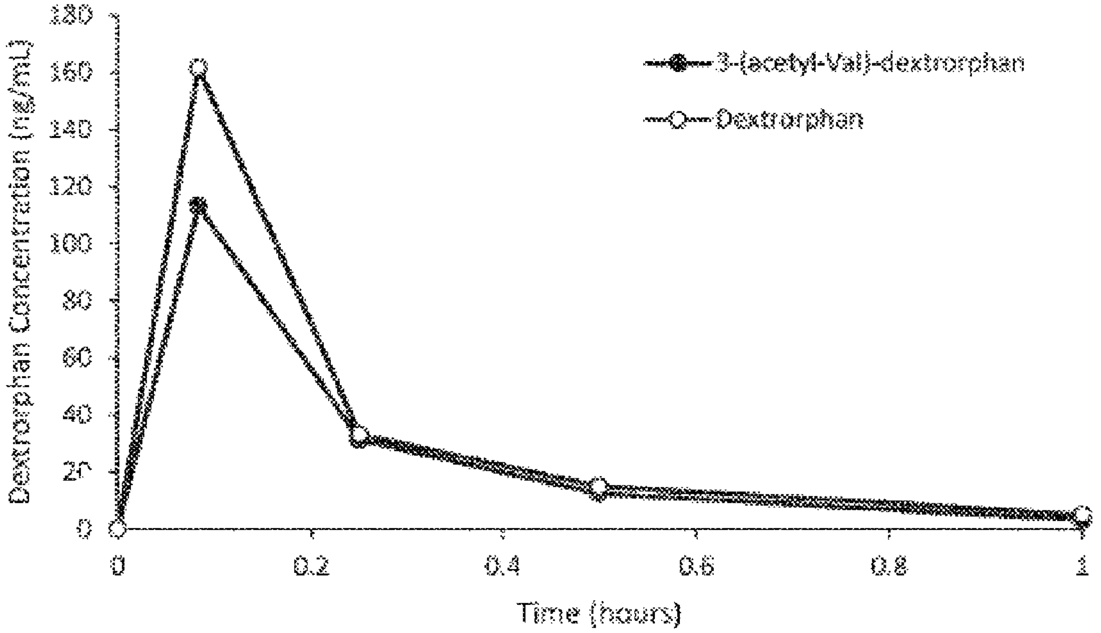
FIG. 17. Intranasal PK curves comparing 3-(N-acetyl-Val)-dextrorphan conjugate with unconjugated dextrorphan in rats.

The present technology provides compositions comprising one or more oxoacids, amino acids, polyethylene glycols and/or vitamin compounds ("ligands") that are chemically conjugated to dextrorphan ((+)-17-methylmorphinan-3-ol) to form novel prodrugs and compositions of dextrorphan. In some embodiments, the chemical bond between the ligands and dextrorphan can be established by reacting the functional group of the ligand, either directly or through a linking group, with one of the following functional groups of dextrorphan:

(a) C-3 hydroxyl of dextrorphan, (b) N-17 tertiary amine of dextrorphan, (c) or both C-3 hydroxyl and N-17 tertiary amine of dextrorphan.

In some embodiments, the chemical bond between the ligands and dextrorphan can be established by reacting the C-3 hydroxyl of dextrorphan with the activated carboxylic acid function of an oxoacid or some vitamin compounds thereby creating an ester conjugate. In other embodiments, the hydroxyl group of an alcohol, hydroxyacid, hydroxyamino acid, or some vitamin compounds are conjugated to the C-3 of dextrorphan via a carbonate bond. In further embodiments, a hydroxyacid is used as a linker that is connected via carbonate bond to the C-3 of dextrorphan on one end (by reaction with its hydroxyl group) and via ester bond to an alcohol, hydroxyacid, hydroxyamino acid, or vitamin compound on the other end (by reaction with its carboxyl group). In yet further embodiments, a dicarboxylic acid is used as a linker that is connected via an ester bond to the C-3 of dextrorphan on one end and via another ester bond to an alcohol, hydroxyacid, hydroxyamino acid, or vitamin compound on the other end. In some embodiments, the chemical bond between the oxoacids, amino acids, polyethylene glycols, and vitamin compounds can be established through an alkylation reaction with the N-17 tertiary amine of dextrorphan to form a quaternary ammonium salt or dextrorphanium salt. In some embodiments, the oxoacids, amino acids, polyethylene glycols, and vitamin compounds are directly connected to this N-alkyl linker via an ester or carbonate bond. In other embodiments, a second linker is attached to the first N-alkyl linker via an ester or carbonate bond. The oxoacids, amino acids, polyethylene glycols, and vitamin compounds are then connected to the second linker via an ester bond. In further embodiments, the second linker may comprise an alcohol, hydroxyacid, or hydroxyamino acid.

The use of "opioid" is meant to include any drug that activates the opioid receptors found in the brain, spinal cord and gut. There are four broad classes of opioids: naturally occurring opium alkaloids, such as morphine (the prototypical opioid) codeine, and thebaine; endogenous opioid peptides, such as endorphins; semi-synthetics such as heroine, oxycodone and hydrocodone that are produced by modifying natural opium alkaloids (opiates) and have similar chemical structures; and pure synthetics such as fentanyl and methadone that are not produced from opium and may have very different chemical structures than the opium alkaloids. Additional examples of opioids are hydromorphone, oxymorphone, methadone, dextrorphan, dihydrocodeine, meperidine, diphenoxylate, sufentanil, alfentanil, propoxyphene, pentazocine, nalbuphine, butorphanol, buprenorphine, meptazinol, dezocine, and pharmaceutically acceptable salts thereof.

The use of the term "dextrorphan" herein means the (+)-isomer of 17-methylmorphinan-3-ol, including all salt forms thereof. In some embodiments, the conjugates contain dextrorphan in a racemic mixture (racemorphan). In other embodiments, the dextrorphan conjugates are not in a racemic mixture. Depending on the chemical structure of the linkers and oxoacids, amino acids, polyethylene glycol (PEG or PEO), and vitamin compounds, as well as the chiral composition of the dextrorphan to which they are attached, the resulting prodrug conjugates can be optically active mixtures of isomers, racemic mixtures, single isomers or combinations thereof.

As used herein, the term "prodrug" refers to a substance converted from an inactive form of a drug to an active drug in the body by a chemical or biological reaction. In the present technology, the prodrug is a conjugate of at least one drug, dextrorphan, and at least one oxoacid, for example. Thus, the conjugates of the present technology are prodrugs and the prodrugs of the present technology are conjugates.

Prodrugs are often useful because, in some embodiments, they may be easier to administer or process than the parent drug. They may, for instance, be more bioavailable by oral administration whereas the parent drug is not. The prodrug may also have improved solubility in pharmaceutical compositions over the parent drug. An embodiment of a prodrug would be a dextrorphan conjugate that is metabolized to reveal the active moiety. In certain embodiments, upon in vivo administration, a prodrug is chemically converted to the biologically, pharmaceutically or therapeutically more active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. The prodrug is designed to alter the metabolism, pharmacokinetics, or the transport characteristics of a drug in certain embodiments, to mask side-effects or toxicity, to improve bioavailability and/or water solubility, to improve the flavor of a drug or to alter other characteristics or properties of a drug in other discrete embodiments.

In some embodiments, the present technology provides at least one prodrug composition comprising at least one conjugate. The at least one conjugate may comprise at least one dextrorphan and at least one oxoacid, amino acid, polyethylene glycol, vitamin compound, or derivatives thereof. In some embodiments, the conjugate further comprises at least one linker. The linker chemically bonds the dextrorphan to the oxoacid, amino acid, polyethylene glycol, or vitamin compound via one or more covalent bonds.

Depending on the linker and the oxoacid, amino acid, polyethylene glycol, and vitamin compound conjugated to dextrorphan or derivative thereof, the at least one prodrug formed can be either a neutral (uncharged), a free acid, a free base or a pharmaceutically acceptable anionic salt form or salt mixtures with any ratio between positive and negative components. These anionic salt forms can include, but are not limited to, for example, acetate, l-aspartate, besylate, bicarbonate, carbonate, d-camsylate, l-camsylate, citrate, edisylate, formate, fumarate, gluconate, hydrobromide/bromide, hydrochloride/chloride, d-lactate, l-lactate, d,l-lactate, d,l-malate, l-malate, mesylate, pamoate, phosphate, succinate, sulfate, bisulfate, d-tartrate, l-tartrate, d,l-tartrate, meso-tartrate, benzoate, gluceptate, d-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate (mucate), galacturonate, gallate, gentisate, glutamate, glutamate, glutarate, glycerophosphate, heptanoate (enanthate), hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, or undecylenate.

Without wishing to be limited to the following theory, it is believed that the prodrugs/conjugates of the present technology undergo enzyme hydrolysis of the ester or carbonate bond, and enzyme hydrolysis of the quaternary ammonium salt in vivo, which subsequently leads to a cascade reaction resulting in rapid regeneration of dextrorphan and the respective oxoacid, amino acid, polyethylene glycol, vitamin compound, or metabolites thereof and/or derivatives thereof. The oxoacids, amino acids, polyethylene glycols, vitamin compounds, or derivatives thereof, of the present technology are non-toxic or have very low toxicity at the given dose levels and are preferably known drugs, natural products, metabolites, or GRAS (Generally Recognized As Safe) compounds (e.g., preservatives, dyes, flavors, etc.) or non-toxic mimetics or derivatives thereof.

General Structures

In some embodiments, the general structure of the conjugates of dextrorphan of the present technology can be represented by the following general Formula IA:

Formula IA

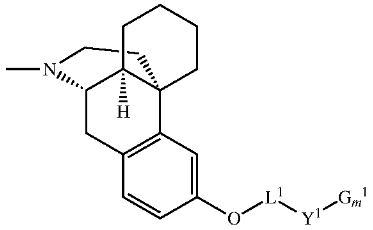

where $L^1$ is absent, or is

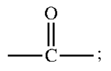

$Y^1$ is absent, or $[A\text{-}X—Z]_n$ where A, X, Z are independently absent or selected from —O—, —S— or $—(CR^1R^2)_k—$ $R^1$, $R^2$ are independently selected from H, alkyl, aryl, alkylaryl, alkoxy, haloalkyl, haloaryl n and k are independently 1-4

$G^1_m$ is absent or selected independently for each repeating subunit from H, amino acid, oxoacid, polyethylene glycol having from 2 to 5 ethylene oxide units, or a vitamin compound, and m is 1-4, except that m is 1 when $G^1$ is a hydrogen atom.

In some embodiments, $L^1$ and $Y^1$ are absent, $G^1$ is an oxoacid, and m is 1-3. Representative examples include, but are not limited to 3-Val-dextrorphan; 3-(ValValPhe)-dextrorphan; 3-(PhePhePhe)-dextrorphan; 3-(AlaAlaVal)-dextrorphan; 3-(GlyGlyAla)-dextrorphan; 3-hippuryl-dextrorphan; 3-(ProProPhe)-dextrorphan; 3-(GlyGly)-dextrorphan; 3-(ValGly)-dextrorphan; 3-(AlaPro)-dextrorphan; 3-cinnamoyl-dextrorphan; 3-(N,O-diacetyl-Tyr)-dextrorphan; and 3-(N-succinoyl-Val)-dextrorphan;

In some embodiments, $L^1$ is present, A and Z are O, X is $—(CR^1R^2)_k—$, and $G^1$ is an oxoacid and m is 1-3. Representative examples include, but are not limited to, 3-(N-acetyl-Val-$OCH_2OC(O)$)-dextrorphan; 3-(cinnamoyl-$OCH_2OC(O)$)-dextrorphan; 3-(benzoyl-$OCH_2OC(O)$-dextrorphan; 3-(butanoyl-$OCH_2OC(O)$)-dextrorphan; 3-(N,O-acetyl-Lys-$OCH_2OC(O)$)-dextrorphan.

In some embodiments, $L^1$ and $Y^1$ are absent, and $G^1$ is a vitamin compound. Representative examples include, but are not limited to, 3-biotinyl-dextrorphan.

In some embodiments, $L^1$ is present, A is O, X and Z are absent, and $G^1$ is a vitamin compound. Representative examples include, but are not limited to, 3-(ascorbyl-C(O))-dextrorphan.

In some embodiments, $L^1$ is present, $Y^1$ is absent, m is 2 and $G^1_m$ can be represented as $G^1$ and $G^2$ where $G^1$ is a hydroxycarboxylic acid, and $G^2$ is a vitamin compound. Representative examples include, but are not limited to 3-(biotinyl-glycoloyl)-dextrorphan.

In some embodiments, $L^1$ is absent, $Y^1$ is absent, m is 2 and $G^1_m$ can be represented as $G^1$ and $G^2$ where $G^1$ is a dicarboxylic acid, and $G^2$ is a vitamin compound. Representative examples include, but are not limited to 3-(thiaminyl-succinoyl)-dextrorphan.

In some embodiments, $L^1$ is present, A is —$CR^1R^2$—, X is absent, Z is —$CR^1R^2$— or absent, and $G^1$ is polyethylene glycol. Representative examples include, but are not limited to 3-($N_3$-$PEG_4$-$CH_2CH_2C$(O))-dextrorphan and 3-($H_2N$-$PEG_5$-$CH_2CH_2C$(O))-dextrorphan.

In some embodiments, $L^1$ is present, A is oxygen, X and Z are —$(CR^1R^2)_k$— and $G^1$ is a hydrogen atom. Representative examples include, but are not limited to, 3-(ethoxy-C(O))-dextrorphan.

In some embodiments, $L^1$ is present, A is —$(CR^1R^2)_k$—, X and Z are absent, and $G^1$ is acetic acid. Representative examples include, but are not limited to 3-(acetyl-$OCH_2C$(O))-dextrorphan and 3-(acetyl-OCH(phenyl)C(O))-dextrorphan.

In some embodiments, the general structure of the conjugates of dextrorphan of the present technology can be represented by the following general Formula IB:

Formula IB

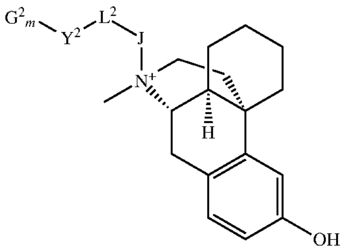

where $L^2$ is absent, or is

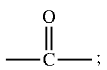

$Y^2$ is absent, or $[A-X—Z]_n$ where A, X, Z are independently absent or selected from —O—, —S— or —$(CR^1R^2)_k$—

J is $[M-W]_p$ where M is —$(CR^3R^4)_q$—; and W is absent, or —O— or —S—

$R^1$, $R^2$, $R^3$, $R^4$ are each independently selected from H, alkyl, aryl, alkylaryl, alkoxy, haloalkyl, haloaryl n and k are independently 1-4 p and q are independently 1-4

$G^2_m$ is absent or selected independently for each repeating subunit from H, amino acid, oxoacid, polyethylene glycol having from 1 to 5 ethylene oxide units, or a vitamin compound, and m is 1-4, except that m is 1 when $G^2$ is a hydrogen atom.

In some embodiments, M is —$(CR^3R^4)_q$—, W, $L^2$ and $Y^2$ are absent, $G^2$ is an oxoacid, and m is 1-3. Representative examples include, but are not limited to N-(acetyl-$OCH_2$)-dextrorphanium; N-(pivaloyl-$OCH_2$)-dextrorphanium; N-(Ser-Ile-$CH_2$)-dextrophanium; N-(Val-$CH_2$)-dextrorphanium; and N-(Phe-Val-$CH_2$)-dextrorphanium.

In some embodiments, M is —$(CR^3R^4)_q$—, W is —O—, $L^2$ is present, A is —$CR^1R^2$—, X is absent, Z is absent or —$CR^1R^2$—, $G^2$ is polyethylene glycol. Representative examples include, but are not limited to N-(MeO-$PEG_3$-$CH_2C(O)OCH_2$)-dextrorphanium and N—(HO-$PEG_4$-$CH_2CH_2C(O)CH_2$)-dextrorphanium.

In some embodiments, M is —$(CR^3R^4)_q$—, W is —O—, $L^2$ is present, A and Z are —O—, X is —$(CR^1R^2)_k$—, $G^2$ is an oxoacid, and m is 1-3. Representative examples include, but are not limited to N—(BzO-$CH_2OC(O)OCH_2$)-dextrorphanium; N-(Ala-$CH_2OC(O)OCH_2$)-dextrorphanium; and N-(Pro-Val-$CH_2OC(O)OCH_2$)-dextrorphanium.

In some embodiments, M is —$(CR^3R^4)_q$—, W is —O—, $L^2$ is present, A is —O—, X and Z are absent, $G^2$ is a vitamin compound, and m is 1-3.

In some embodiments, the general structure of the conjugates of dextrorphan of the present technology can be represented by the following general Formula IC:

Formula IC

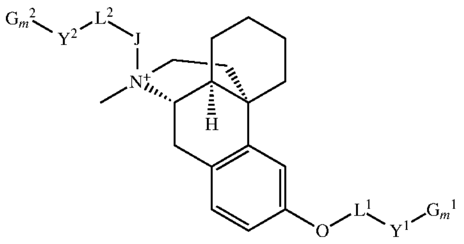

where $L^1$ and $L^2$ are independently absent, or is

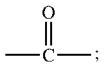

$Y^1$ and $Y^2$ are independently either absent, or $[A-X—Z]_n$ where A, X, Z are independently selected for $Y^1$ and $Y^2$, and are independent of each other either absent or selected from the group of —O—, —S—, or —$(CR^1R^2)_k$—

J is $[M-W]_p$ where M is —$(CR^3R^4)_q$—; and W is absent, or —O— or —S—

$R^1$, $R^2$, $R^3$, $R^4$ are each independently selected for $Y^1$ and $Y^2$, and are independent of each other selected from the group of H, alkyl, aryl, alkylaryl, alkoxy, haloalkyl, haloaryl For each $Y^1$ and $Y^2$, n is independently an integer of 1-4.

For each repeating unit of $[A-X—Z]_n$, k is independently an integer of 1-4.

p and q are independently 1-4

$G^1_m$ and $G^2_m$ are independently absent, or selected independently of each other and for each repeating subunit from H, amino acid, oxoacid, polyethylene glycol having from 2 to 5 ethylene oxide units, or a vitamin compound;

where m is selected independently for $G^1$ and $G^2$, and is an integer of 1-4, except that m is 1 when $G^1$ or $G^2$ is a hydrogen atom.

In some embodiments, $L^1$ and $Y^1$ are absent, $G^1$ is an oxoacid and m is 1-3, and M is $—(CR^3R^4)_q—$; W, $L^2$ and $Y^2$ are absent, $G^2$ is an oxoacid, and m is 1-3. Representative examples include 3-(pivaloyl)-N-(pivaloyl-$OCH_2$)-dextrorphanium; 3-(Ac-Val)-N-(Phe-Phe-$CH_2$)-dextrorphanium; 3-(Ser-Ile)-N-(Val-$CH_2$)-dextrorphanium; 3-Val-N-(Val-$CH_2$)-dextrorphanium;

In some embodiments, $L^1$ and $Y^1$ are present, A is O, X is $—(CR^1R^2)_k—$, Z is O, $G^1_m$ an oxoacid, and m is 1-3, and M is $—(CR^3R^4)_q—$; W, $L^2$ and $Y^2$ are absent, $G^2$ is an oxoacid, and m is 1-3. Representative examples include 3-(acetylsalicyloyl-$OCH_2OC(O)$)—N-(Ac-Val-$CH_2$)-dextrorphanium.

In some embodiments, $L^1$ is present, $Y^1$ is present, where A is $—(CR^1R^2)_k—$, X and Z are absent, and $G^1$ is H, and M is $—(CR^3R^4)_q—$, W is O, $L^2$ and $Y^2$ are absent, $G^2$ is an oxoacid, and m is 1-3. Representative examples include 3-acetyl-N-(acetyl-$OCH_2$)-dextrorphanium.

In some embodiments, $L^1$ is present, $Y^1$ is present, where A is O, X and Z are $—(CR^1R^2)_k—$, and $G^1$ is H, and M is $—(CR^3R^4)_q—$, W is O, $L^2$ and $Y^2$ are present, where A is O, X and Z are $—(CR^1R^2)_k—$, and $G^2$ is H. Representative examples include 3-(ethoxy-C(O))—N-(ethoxy-C(O)CH($CH_3$))-dextrorphanium.

Oxoacids

Organic oxoacids (i.e., oxyacids, oxo acids, oxy-acids, oxiacids, oxacids) of the present technology are a class of compounds which contain oxygen, at least one other element, and at least one hydrogen bound to oxygen, and which produce a conjugate base by loss of positive hydrogen ion(s) (protons). Organic acids include carboxylic acids. Carboxylic acids are widespread in nature (naturally occurring), but carboxylic acids can also be non-natural (synthetic). Carboxylic acids can be categorized into numerous classes based on their molecular structure or formula, and many of the different classes may overlap.

Without wishing to limit the scope to one classification, the carboxylic acids of the present technology can be grouped into the following categories: aryl carboxylic acids, aliphatic carboxylic acids, dicarboxylic, polycarboxylic acids, and amino acids.

Some embodiments of the present technology provide oxoacids conjugated to dextrorphan, where the carboxylic acid group is directly attached to an aryl moiety. Carboxylic acids directly attached to the aryl moiety include benzoates and heteroaryl carboxylic acids. Benzoates are common in nature and include, for example but are not limited to, aminobenzoates (e.g., anthranilic acid analogs such as fenamates), aminohydroxybenzoates and hydroxybenzoates (e.g., salicylic acid analogs).

The general structure of benzoic acid and benzoic acid derivatives of the present technology can be represented by the following Formula II:

Formula II

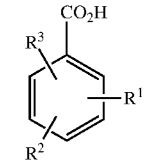

In this Formula II, $R^1$, $R^2$, $R^3$ are independently selected from the group consisting of H, hydroxyl, amino, amine, amide, thiol, cyano, nitro, halogen, imine, alkyl, alkoxy, aryl, alkenyl, alkynyl, haloalkyl, alkylaryl, arylalkyl, heterocycle, arylalkoxy, cycloalkyl, cycloalkenyl, cycloalkynyl, carbonyl, thioether, selenoether, silyl, silyloxy, sulfonyl, phosphonate.

Suitable hydroxyobenzoic acids can be found in FIG. 1 and include, but are not limited to, benzoic acid, salicylic acid, acetylsalicylic acid (aspirin), 3-hydroxybenzoic acid, 4-hydroxybenzoic acid, 6-methylsalicylic acid, o,m,p-cresotinic acid, anacardic acids, 4,5-dimethylsalicylic acid, o,m,p-thymotic acid, diflunisal, o,m,p-anisic acid, 2,3-dihydroxybenzoic acid (2,3-DHB), α,β,γ-resorcylic acid, protocatechuic acid, gentisic acid, piperonylic acid, 3-methoxysalicylic acid, 4-methoxysalicylic acid, 5-methoxysalicylic acid, 6-methoxysalicylic acid, 3-hydroxy-2-methoxybenzoic acid, 4-hydroxy-2-methoxybenzoic acid, 5-hydroxy-2-methoxybenzoic acid, vanillic acid, isovanillic acid, 5-hydroxy-3-methoxybenzoic acid, 2,3-dimethoxybenzoic acid, 2,4-dimethoxybenzoic acid, 2,5-dimethoxybenzoic acid, 2,6-dimethoxybenzoic acid, veratric acid (3,4-dimethoxybenzoic acid), 3,5-dimethoxybenzoic acid, gallic acid, 2,3,4-trihydroxybenzoic acid, 2,3,6-trihydroxybenzoic acid, 2,4,5-trihydroxybenzoic acid, 3-O-methylgallic acid (3-OMGA), 4-O-methylgallic acid (4-OMGA), 3,4-O-dimethylgallic acid, syringic acid, 3,4,5-trimethoxybenzoic acid.

Suitable aminobenzoic acids are shown in FIG. 2 and include, but are not limited to, anthranilic acid, 3-aminobenzoic acid, 4,5-dimethylanthranilic acid, N-methylanthranilic acid, N-acetylanthranilic acid, fenamic acids (e.g., tolfenamic acid, mefenamic acid, flufenamic acid), 2,4-diaminobenzoic acid (2,4-DABA), 2-acetylamino-4-aminobenzoic acid, 4-acetylamino-2-aminobenzoic acid, 2,4-diacetylaminobenzoic acid.

Suitable aminohydroxybenzoic acids include, but are not limited to, 4-aminosalicylic acid, 3-hydroxyanthranilic acid, 3-methoxyanthranilic acid.

In some embodiments, the composition includes a benzoate conjugate comprising at least one dextrorphan conjugated to at least one benzoic acid or benzoic acid derivative, salt thereof or combination thereof.

In some embodiments, the benzoates include numerous benzoic acid analogs, benzoate derivatives with hydroxyl or amino groups or a combination of both. The hydroxyl and amino functions may be present in their free form or capped with another chemical moiety, preferably but not limited to methyl or acetyl groups. The phenyl ring may have additional substituents, but the total number of substituents can be four or less, three or less, or two or less.

In yet another embodiment, the present technology provides a prodrug or composition comprising at least one conjugate of dextrorphan and at least one heteroaryl carboxylic acid, a derivative thereof, or a combination thereof. The heteroaryl carboxylic acid can be selected from Formula III, Formula IV, Formula V, Formula VI, Formula VII, Formula VIII, Formula IX, Formula X, or Formula XI, where Formula III, Formula IV, Formula V, Formula VI, Formula VII, Formula VIII, Formula IX, Formula X, or Formula XI are:

Formula III

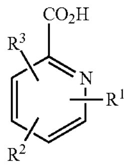

Formula IV

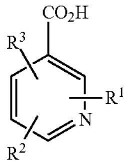

Formula V

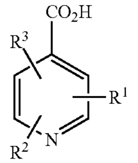

Formula VI

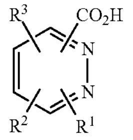

Formula VII

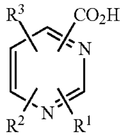

Formula VIII

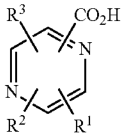

Formula IX

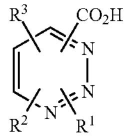

Formula X

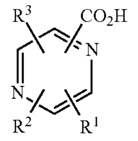

Formula XI

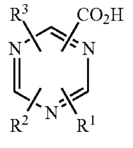

For these Formulas III, IV, V, VI, VII, VIII, IX, X, and XI, $R^1$, $R^2$, $R^3$ are independently selected from the group consisting of H, hydroxyl, amino, amine, amide, thiol, cyano, nitro, halogen, imine, alkyl, alkoxy, aryl, alkenyl, alkynyl, haloalkyl, alkylaryl, arylalkyl, heterocycle, arylalkoxy, cycloalkyl, cycloalkenyl, cycloalkynyl, carbonyl, thioether, selenoether, silyl, silyloxy, sulfonyl, phosphonate. Some structures of suitable heteroaryl carboxylic acids for use in the present technology are found in FIG. 3.

In some embodiments, the carboxy group of the aryl carboxylic acids can be attached directly to the aromatic ring. The present technology includes both carbon-only aryl groups and aryl groups with heteroatoms (heteroaryl). The aryl or heteroaryl group which is connected directly to the carboxyl function can be a 6-membered ring and contains no or one heteroatom. In some embodiments, the additional substituted or unsubstituted aromatic or aliphatic rings can be fused to this 6-membered aryl or heteroaryl moiety. In some embodiments, the aryl carboxylic acids may have only one free carboxylic acid group and the total number of phenyl substituents on the 6-membered ring should be four or less, for example, 4, 3, 2 or 1.

Phenylacetates

In some embodiments of the present technology, the aryl carboxylic acids of the present technology comprise a carboxylic group that is separated by one carbon from the aryl moiety. These aryl carboxylic acids include branched phenylpropionic acids (i.e., 2-methyl-2-phenylacetates) or other derivatives of phenylacetate (FIG. 4). The general structure of at least one phenylacetate of the present technology is represented by the following general Formula XII:

Formula XII

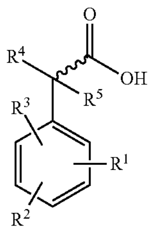

For this Formula XII, $R^1$, $R^2$, $R^3$, $R^4$, $R^5$ are independently selected from the group consisting of H, hydroxyl, amino, amine, amide, thiol, cyano, nitro, halogen, imine, alkyl, alkoxy, aryl, alkenyl, alkynyl, haloalkyl, alkylaryl, arylalkyl, heterocycle, arylalkoxy, cycloalkyl, cycloalkenyl, cycloalkynyl, carbonyl, thioether, selenoether, silyl, silyloxy, sulfonyl, phosphonate.

Phenylacetic acids encompass various subsets of natural products, metabolites and pharmaceuticals. One such pharmaceutically important subset is "profens", a type of NSAIDs and derivatives of certain phenylpropionic acids (e.g., 2-methyl-2-phenylacetic acid analogs). Some other phenylacetates have central functions in the phenylalanine and tyrosine metabolism.

Some examples of phenylacetates of the present technology include, but are not limited to, phenylacetic acid (hydratropic acid), 2-hydroxyphenylacetic acid, 3-hydroxyphenylacetic acid, 4-hydroxyphenylacetic acid, homoprotocatechuic acid, homogentisic acid, 2,6-dihydroxyphenylacetic acid, homovanillic acid, homoisovanillic acid, homoveratric acid, atropic acid, d,l-tropic acid, diclofenac, d,l-mandelic acid, 3,4-dihydroxy-d,l-mandelic acid, vanillyl-d,l-mandelic acid, isovanillyl-d,l-mandelic acid, ibuprofen, fenoprofen, carprofen, flurbiprofen, ketoprofen, and naproxen. Some structures of suitable phenylacetates for use in the present technology are found in FIG. 4.

Benzylacetates

In additional embodiments, the aryl carboxylic acids of the present technology comprise a carboxylic group that is separated by two carbons from the aryl moiety. These aryl carboxylic acids include benzylacetates (FIG. 5) and substituted derivatives thereof and analogs of cinnamic acid (FIG. 6). Both classes of compounds are abundant in nature in the form of natural products or metabolites (e.g., phenylalanine metabolism). The general structures of some benzylacetates and cinnamates of the present technology are represented by the following general Formulas XIII and XIV:

Formula XIII

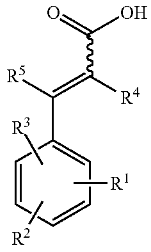

Formula XIV

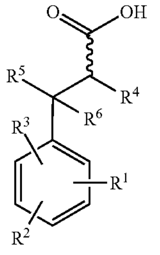

For these Formulas XIII and XIV, $R^1$, $R^2$, $R^3$, $R^4$, $R^5$, $R^6$ are independently selected from the group consisting of H, hydroxyl, amino, amine, amide, thiol, cyano, nitro, halogen, imine, alkyl, alkoxy, aryl, alkenyl, alkynyl, haloalkyl, alkylaryl, arylalkyl, heterocycle, arylalkoxy, cycloalkyl, cycloalkenyl, cycloalkynyl, carbonyl, thioether, selenoether, silyl, silyloxy, sulfonyl, phosphonate.

Benzylacetic acids are defined by an ethylene group between the carboxyl function and the phenyl ring. Both the alkyl chain and the aryl moiety can have substituents, preferably hydroxyl groups. Some compounds of this class can be found in the phenylalanine metabolism.

Some examples of benzylacetates of the present technology include, but are not limited to, benzylacetic acid, melilotic acid, 3-hydroxyphenylpropanoic acid, 4-hydroxyphenylpropanoic acid, 2,3-dihydroxyphenylpropanoic acid, d,l-phenyllactic acid, o,m,p-hydroxy-d,l-phenyllactic acid, phenylpyruvic acid.

Cinnamates

Cinnamic acids (3-phenylacrylic acids) (FIG. 6) are unsaturated analogs of benzylacetic acids. Cinnamates occur in two isomeric forms: cis (Z) and trans (E). The cinnamate isomers of certain embodiments of the present technology are preferably, but not limited to, the trans configuration. Similar to benzylacetates, derivatives of cinnamic acid can be substituted on the alkenyl or aryl moiety of the molecule. Preferred substituents of some embodiments of the present technology are hydroxyl and methoxy groups. Certain cinnamates are thought to play a key role in phenylalanine metabolism.

Some examples of cinnamates of the present technology include, but are not limited to, cinnamic acid, o,m,p-coumaric acid, 2,3-dihydroxycinnamic acid, 2,6-dihydroxycinnamic acid, caffeic acid, ferulic acid, isoferulic acid, 5-hydroxyferulic acid, sinapic acid, 2-hydroxy-3-phenylpropenoic acid.

Suitable aliphatic carboxylic acids for use in the present technology include, but are not limited to, for example, saturated, monounsaturated, polyunsaturated, acetylenic, substituted (e.g., alkyl, hydroxyl, methoxy, halogenated, etc.), heteroatom containing or ring containing carboxylic acids. Suitable examples of saturated carboxylic acids include, but are not limited to, for example, methanoic, ethanoic, propanoic, butanoic, pentanoic, hexanoic, heptanoic, octanoic, 2-propylpentanoic acid, nonanoic, decanoic, dodecanoic, tetradecanoic, hexadecanoic, heptadecanoic, octadecanoic, or eicosanoic acid. Suitable monounsaturated carboxylic acids for practice of the present technology include, but are not limited to, for example, 4-decenoic, 9-decenoic, 5-lauroleic, 4-dodecenoic, 9-tetradecenoic, 5-tetradecenoic, 4-tetradecenoic, 9-hexadecenoic, 6-hexadecenoic, 6-octadecenoic, or 9-octadecenoic acid.

Suitable polyunsaturated carboxylic acids for use in the present technology include, but are not limited to, for example, sorbic, octadecadienoic, octadecatrienoic, octadecatetraenoic, eicosatrienoic, eicosatetraenoic, eicosapentaenoic, docosapentaenoic, or docosahexaenoic acids. Suitable acetylenic carboxylic acids for use in the present technology include, but are not limited to octadecynoic, octadecenynoic, 6,9-octadecenynoic, heptadecenynoic, tridecatetraenediynoic, tridecadienetriynoic, octadecadienediynoic, heptadecadienediynoic, octadecadienediynoic, octadecenediynoic, or octadecenetriynoic acids.

Suitable substituted carboxylic acids for practice of the present technology include, but are not limited to, for example, methylpropanoic, isovaleric, methylhexadecanoic, 8-methyl-6-nonenoic, methyloctadecanoic, trimethyloctacosanoic, trimethyltetracosenoic, heptamethyltriacontanoic, tetramethylhexadecanoic, tetramethylpentadecanoic, lactic, glyceric, glycolic, threonic, 3-hydroxypropionic, hydroxyoctadecatrienoic, hydroxyoctadecenoic, hydroxytetracosanoic, 2-hydroxybutyric, 3-hydroxybutyric, 4-hydroxybutyric, 4-hydroxypentanoic, hydroxyoctadecadienediynoic, hydroxyoctadecadienoic, 10-hydroxydecanoic, hydroxydecenoic, hydroxyeicosenoic, hydroxyeicosadienoic, hydroxyhexadecanoic, dihydroxytetracosenoic, dihydroxydocosanoic, hydroxydocosanoic, trihydroxyoctadecanoic, trihydroxyhexadecanoic, trihydroxyicosahexaenoic, trihydroxyicosapentaenoic, 2-methoxy-5-hexadecenoic, 2-methoxy hexadecanoic, 7-methoxy-4-tetradecenoic, 9-methoxypentadecanoic, 11-methoxyheptadecanoic, 3-methoxydocosanoic, diacetoxydocosanoic, 2-acetoxydocosanoic, 2-acetoxytetracosanoic, 2-acetoxyhexacosanoic, 9-oxononanoic, oxodecanoic, oxododecenoic, hydroxyoxodecenoic, 10-oxo-8-decenoic, fluorooctadecenoic, fluorodecanoic, fluorotetradecanoic, fluorohexadecanoic, fluorooctadecadienoic, chlorohydroxyhexadecanoic, chlorohydroxyoctadecanoic, dichlorooctadecanoic, 3-bromo-2-nonaenoic, 9,10-dibromooctadecanoic, 9,10,12,13-tetrabromooctadecanoic, 10-nitro-9,12-octadecadienoic, 12-nitro-9,12-octadecadienoic, 9-nitro-9-octadecenoic, 9-oxo-2-decenoic, 9-oxo-13-octadecenoic, oxooctadecatrienoic, 15-oxo-18-tetracosenoic, 17-oxo-20-hexacosenoic, or 19-oxo-22-octacosenoic acids.

Suitable examples of heteroatom containing carboxylic acids include, but are not limited to, for example, 9-(1,3-nonadienoxy)-8-nonenoic, 9-(1,3,6-nonatrienoxy)-8-nonenoic, 12-(1-hexenoxy)-9,11-dodecadienoic, 12-(1,3-hexadienoxy)-9,11-dodecadienoic, 2-dodecylsulfanylacetic, 2-tetradecylsulfanylacetic, 3-tetradecylsulfanylprop-2-enoic, or 3-tetradecylsulfanylpropanoic acid. Suitable examples of ring containing carboxylic acids include, but are not limited to, for example, 10-(2-Hexylcyclopropyl) decanoic, 3-(2-[6-bromo-3,5-nondienylcyclopropyl)propanoic, 9-(2-hexadecylcyclopropylidene)non-5-enoic, 8-(2-octyl-1-cyclopropenyl)octanoic, 7-(2-octyl-1-cyclopropenyl)heptanoic, 9,10-epoxyoctadecanoic, 9,10-epoxy12-octadecenoic, 12,13-epoxy-9-octadecenoic, 14,15-epoxy-11-eicosenoic, 11-(2-cyclopenten-1-yl)undecanoic, 13-(2-cyclopenten-1-yl)tridecanoic, 13-(2-cyclopentenyl)-6-tridecenoic, 11-cyclohexylundecanoic, 13-cyclohexyltridecanoic, 7-(3,4-dimethyl-5-pentylfuran-2-yl)heptanoic, 9-(4-methyl-5-pentylfuran-2-yl)nonanoic, 4-[5]-ladderane-butanoic, 6-[5]-ladderane-hexanoic, or 6-[3]-ladderane-hexanoic acid.

In some embodiments, the dextrorphan, derivatives thereof or combinations thereof, can be conjugated to one or more dicarboxylic acids or tricarboxylic acids. Dicarboxylic acids are compounds with two carboxyl groups with a general formula of HOOC—R—COOH, where R can be an alkyl, alkenyl, alkynyl or aryl group, or derivatives thereof. Dicarboxylic acids can have straight carbon chains or branched carbon chains. The carbon chain length may be short or long. Polycarboxylic acids are carboxylic acids with three or more carboxyl groups. Suitable examples of dicarboxylic and tricarboxylic acids for the practice of the present technology include, but are not limited to, for example, oxalic, malonic, succinic, glutaric, adipic, pimelic, suberic, azelaic, sebacic, brassylic, thapsic, malic, tartaric, dihydroxymesoxalic, α-hydroxyglutaric, methylmalonic, meglutol, diaminopimelic, carbamoyl aspartic, fumaric, maleic, mesaconic, 3-methylglutaconic, traumatic, phthalic acid, isophthalic, terephthalic, dipicolinic, citric acid, isocitric, carballylic, or trimesic acid. Some structures of suitable dicarboxylic acids for use in the practice of the present technology can be found in FIG. 7, and some structures of suitable tricarboxylic acids for use in the practice of the present technology can be found in FIG. 8.

Amino Acids

Amino acids are one of the most important building blocks of life. They constitute the structural subunit of proteins, peptides, and many secondary metabolites. In addition to the 22 standard (proteinogenic) amino acids that make up the backbone of proteins, there are hundreds of other natural (non-standard) amino acids that have been discovered either in free form or as components in natural products. The amino acids used in some embodiments of the prodrugs of this invention include natural amino acids, synthetic (non-natural, unnatural) amino acids, and their derivatives.

Standard Amino Acids

There are currently 22 known standard or proteinogenic amino acids that make up the monomeric units of proteins and are encoded in the genetic code. The standard amino acids include alanine, arginine, asparagine, aspartic acid, cysteine, glutamic acid, glutamine, glycine, histidine, isoleucine, leucine, lysine, methionine, phenylalanine, proline, pyrrolysine, selenocysteine, serine, threonine, tryptophan, tyrosine and valine. These standard amino acids have the general structure shown in FIG. 9, where R represents the side chain on the α-carbon.

Non-Standard Amino Acids

Non-standard amino acids can be found in proteins created by chemical modifications of standard amino acids already incorporated in the proteins. This group also includes amino acids that are not found in proteins but are still present in living organisms either in their free form or bound to other molecular entities. Non-standard amino acids occur mostly as intermediates in metabolic pathways of standard amino acids and are not encoded by the genetic code. Examples of non-standard amino acids include but are not limited to ornithine, homoarginine, citrulline, homocitrulline, homoserine, theanine, γ-aminobutyric acid, 6-aminohexanoic acid, sarcosine, cartinine, 2-aminoadipic acid, pantothenic acid, taurine, hypotaurine, lanthionine, thiocysteine, cystathionine, homocysteine, β-amino acids such as β-alanine, β-aminoisobutyric acid, β-leucine, β-lysine, β-arginine, β-tyrosine, β-phenylalanine, isoserine, β-glutamic acid, β-tyrosine, β-dopa (3,4-dihydroxy-L-phenylalanine), α,α-disubstituted amino acids such as 2-aminoisobutyric acid, isovaline, di-n-ethylglycine, N-methyl acids such as N-methyl-alanine, L-abrine, hydroxy-amino acids such as 4-hydroxyproline, 5-hydroxylysine, 3-hydroxyleucine, 4-hydroxyisoleucine, 5-hydroxy-L-tryptophan, cyclic amino acids such as 1-aminocyclopropyl-1-carboxylic acid, azetidine-2-carboxylic acid and pipecolic acid. Some structures of suitable non-standard amino acids that can be used in some embodiments of the prodrugs of this invention are shown in FIG. 10.

Synthetic Amino Acids

Synthetic amino acids do not occur in nature and are prepared synthetically. Examples include but are not limited to allylglycine, cyclohexylglycine, N-(4-hydroxyphenyl) glycine, N-(chloroacetyl)glycline ester, 2-(trifluoromethyl)-phenylalanine, 4-(hydroxymethyl)-phenylalanine, 4-amino-phenylalanine, 2-chlorophenylglycine, 3-guanidino propionic acid, 3,4-dehydro-proline, 2,3-diaminobenzoic acid, 2-amino-3-chlorobenzoic acid, 2-amino-5-fluorobenzoic acid, allo-isoleucine, tert-leucine, 3-phenylserine, isoserine, 3-aminopentanoic acid, 2-amino-octanedioic acid, 4-chloro-β-phenylalanine, β-homoproline, β-homoalanine, 3-amino-3-(3-methoxyphenyl)propionic acid, N-isobutyryl-cysteine, 3-amino-tyrosine, 5-methyl-tryptophan, 2,3-diaminopropionic acid, 5-aminovaleric acid, and 4-(dimethylamino)cinnamic acid. Some structures of suitable synthetic amino acids that can be used in some embodiments of the prodrugs of this invention are shown in FIG. 11.

In some embodiments of the present technology, dextrorphan, derivatives thereof or combinations thereof, is conjugated to a polyethylene glycol, or derivatives thereof. In some embodiments, the terminal hydroxyl group of the polyethylene glycol can be substituted with an amino, azide, or methoxy group. Some suitable structures of polyethylene glycols include the following:

G =

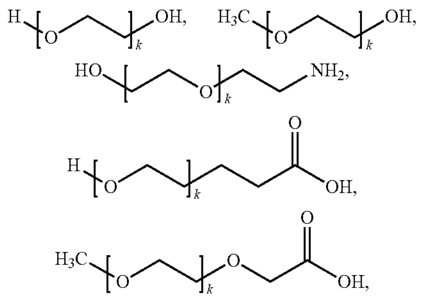

-continued

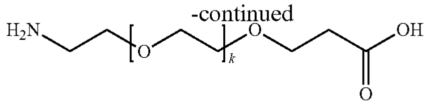

or

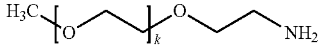

wherein k is 1-20.

Vitamin Compounds

In some embodiments of the present technology, dextrorphan, derivatives thereof, or combinations thereof, is conjugated to one or more vitamin compounds. The vitamin compounds include both water soluble and fat soluble vitamins or derivatives thereof. Useful vitamin compounds are those that have one or more carboxylic acid groups, one or more hydroxyl groups, or one or more other reactive functional groups that can form an ester or carbonate bond with dextrorphan either directly or through one or more linkers. Examples of water soluble vitamins that could be conjugated to dextrorphan include biotin, folate (folic acid), niacin, pantothenic acid, riboflavin, thiamin, pyridoxine, and ascorbic acid. Examples of fat soluble vitamins that could be conjugated to dextrorphan include Vitamin A (retinol), vitamin D2 (ergocalciferol), vitamin D3 (cholecalciferol), vitamin E (tocopherols and tocotrienols, including alpha, beta, gamma, and delta-tocopherol), and vitamin K (phylloquinone). Some structures of suitable water soluble vitamins and fat soluble vitamins for use in the present technology are found in FIGS. 12A and 12B, respectively.

Linkers

In some embodiments of the present technology, the dextrorphan, derivatives thereof, or combinations thereof, is conjugated to one or more organic oxoacids, amino acids, polyethylene glycols, or vitamin compounds via one or more linkers. Linker moieties of the present technology, which connect the one or more organic oxoacids, amino acids, polyethylene glycols, or vitamin compounds to the dextrorphan, derivatives thereof or combinations thereof, can have the following general formulas:

—C(O)O—X—O— or —C(O)X—O—X or —C(O)O—X— or C(O)X—O— for conjugation at the C-3 hydroxyl position;

—X— or —X—O— for conjugation at the N-17 tertiary amine position;

wherein X is selected from a representative group including alkyl, substituted alkyl, aryl, substituted aryl, arylalkyl, substituted alkylaryl, heteroalkyl, substituted heteroalkyl, heteroaryl, substituted heteroaryl, heterocycle, substituted heterocycle, alkenyl, substituted alkenyl, alkynyl, substituted alkynyl, cycloalkyl, substituted cycloalkyl, cycloalkenyl, substituted cycloalkenyl, cycloalkynyl, or substituted cycloalkynyl.

Preferred embodiments of the present technology include linkers where X is at least one aliphatic group. More preferred embodiments include linkers where X is at least one alkyl group.

Physiological Benefits

The above defined prodrugs of dextrorphan can be given orally and, upon administration, release the active dextrorphan after being hydrolyzed in the body. Since the oxoacids, amino acids, polyethylene glycols, and vitamin compounds of this invention are naturally occurring metabolites or mimetics thereof or pharmaceutically active compounds, these prodrugs can be easily recognized by physiological systems resulting in hydrolysis and release of dextrorphan. The claimed prodrugs themselves are either not or have limited pharmacological activity and consequently may follow a metabolic pathway that differs from the parent drug. By choosing suitable oxoacids, amino acids, polyethylene glycols, and vitamin compounds ("ligands") the release of dextrorphan into the systemic circulation can be controlled even when the prodrug is administered via routes other than oral. In one embodiment, the modified dextrorphan would release dextrorphan similar to free or unmodified dextrorphan. In another embodiment, the modified dextrorphan would be released in a controlled or sustained manner. This controlled release can potentially alleviate certain side-effects and improve upon the safety profile of the parent drug. These side-effects may include, dizziness, lightheadedness, drowsiness, nausea, vomiting, constipation, stomach pain, rash, difficulty urinating, difficulty breathing and fainting. In addition, dextrorphan and other opioids (opiates) are also highly addictive and prone to substance abuse.

Recreational drug abuse of opioids is a common problem and usually begins with oral doses taken with the purpose of achieving euphoria ("rush", "high"). Over time the drug abuser often increases the oral dosages to attain more powerful "highs" or to compensate for heightened opioid tolerance. Rapid metabolism and fast duration of action of dextrorphan, contributes to its likelihood of being abused. This behavior can escalate and result in exploring of other routes of administration such as intranasal ("snorting") and intravenous ("shooting"). In some embodiments, dextrorphan that is conjugated with a suitable ligand exhibits no rapid spikes in blood levels after oral administration that is sought by a potential drug abuser. These prodrugs may have a delayed $T_{max}$ and possibly lower $C_{max}$ than the parent drug and therefore lack the feeling of a "rush" when taken orally even at higher doses while still maintaining pain relief. In another embodiment, dextrorphan conjugated with appropriate ligands of this invention is not hydrolyzed efficiently when administered via non-oral routes. As a result, they do not generate high plasma or blood concentrations of released dextrorphan when injected or snorted compared to free dextrorphan administered through these routes. Furthermore, since the ligands of this invention are bound covalently to dextrorphan, the opioid is not liberated by any type of physical manipulation as it is possible, for example, by grinding up or crushing of certain kinds of formulated dextrorphan.

Opioid induced constipation is a common side effect of pain treatment with opioids. It affects approximately 40-90% of the patients who are chronically taking opioid medication. Additionally, patients suffering from OIC may become resistant to laxative treatments. Although the mechanism is not yet fully understood, it is assumed that the binding of agonists to the peripheral μ-opioid receptors in the gastrointestinal (GI) tract is the primary cause of OIC. This opioid receptor activation impairs the coordination of the GI function by the enteric nervous system (ENS) resulting in decreased gut motility by delaying the transit time of fecal content through interference with the normal tone and contractility of the bowels. While the contractions of the circular muscles are increased causing non-propulsive kneading and churning (stasis) and increased fluid absorption, the longitudinal smooth muscle tone is decreased causing reduced forward peristalsis and additional time for desiccating fecal matter. Furthermore, the anal sphincter tone is increased making defecation more difficult. The clinical presentation of these effects typically manifests itself in symptoms of hard/dry stool, straining, incomplete evacuation, bloating and abdominal distention.

In one embodiment, the prodrugs of this invention have no or insignificant activity at the μ-opioid receptors. In another embodiment, they are not subjected to enzymatic hydrolysis until they are absorbed in the gut. Consequently, the active dextrorphan is effectively "cloaked" by the attached ligand and may bypass the peripheral μ-opioid receptors without affecting the ENS thereby reducing or preventing OIC.

Synthetic Schemes

In some embodiments, one or more protecting groups may be attached to any additional reactive functional groups that may interfere with the coupling to dextrorphan. Any suitable protecting group may be used depending on the type of functional group and reaction conditions. Some protecting group suitable for use in the present technology include, but are not limited to, acetyl (Ac), tert-butyoxycarbonyl (Boc), benzyloxycarbonyl (Cbz), p-methoxybenzylcarbonyl (Moz), 9-fluorenylmethyloxycarbonyl (Fmoc), benzyl (Bn), p-methoxybenzyl (PMB), 3,4 dimethoxybenzyl (DMPM), p-methozyphenyl (PMP), tosyl (Ts), or amides (like acetamides, pthalamides, and the like).

In other embodiments, a base may be required at any step in the synthetic scheme of prodrugs of dextrorphan of this invention. Suitable bases include, but are not limited to, 4-methylmorpholine (NMM), 4-(dimethylamino)pyridine (DMAP), N,N-diisopropylethylamine, lithium bis(trimethylsilyl)amide, lithium diisopropylamide (LDA), any alkali metal tert.-butoxide (e.g., potassium tert.-butoxide), any alkali metal hydride (e.g., sodium hydride), any alkali metal alkoxide (e.g., sodium methoxide), triethylamine or any other tertiary amine.

Suitable solvents that can be used for any reaction at any step in the synthetic scheme of a prodrug of dextrorphan of this invention include, but are not limited to, acetone, acetonitrile, butanol, chloroform, dichloromethane, dimethylformamide (DMF), dimethylsulfoxide (DMSO), dioxane, ethanol, ethyl acetate, diethyl ether, heptane, hexane, methanol, methyl tert.-butyl ether (MTBE), isopropanol, isopropyl acetate, diisopropyl ether, tetrahydrofuran, toluene, xylene or water.

In some embodiments, an acid may be used to remove certain protecting groups. Suitable acids include, but are not limited to, hydrochloric acid, hydrobromic acid, hydrofluoric acid, hydriodic acid, sulfuric acid, phosphoric acid, trifluoroacetic acid, acetic acid, citric acid, methanesulfonic acid, p-toluenesulfonic acid and nitric acid. For certain other protecting groups, a catalytic hydrogenation may be used, e.g., palladium on charcoal in the presence of hydrogen gas.

Scheme 1

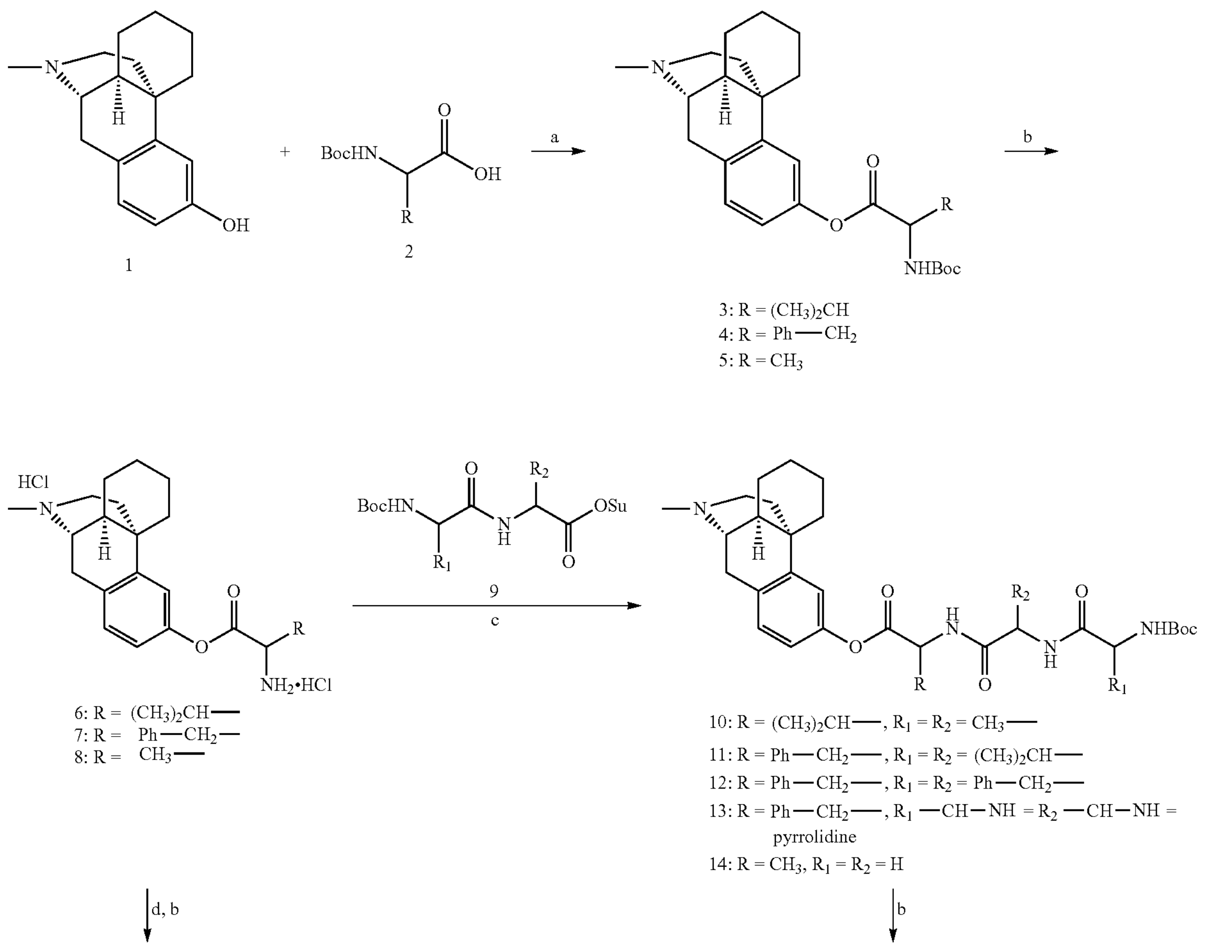

1

2

3: R = $(CH_3)_2CH$
4: R = Ph—$CH_2$
5: R = $CH_3$

9

6: R = $(CH_3)_2CH$—
7: R = Ph—$CH_2$—
8: R = $CH_3$—

10: R = $(CH_3)_2CH$—, $R_1$ = $R_2$ = $CH_3$—
11: R = Ph—$CH_2$—, $R_1$ = $R_2$ = $(CH_3)_2CH$—
12: R = Ph—$CH_2$—, $R_1$ = $R_2$ = Ph—$CH_2$—
13: R = Ph—$CH_2$—, $R_1$ —CH—NH = $R_2$ —CH—NH = pyrrolidine
14: R = $CH_3$, $R_1$ = $R_2$ = H -continued

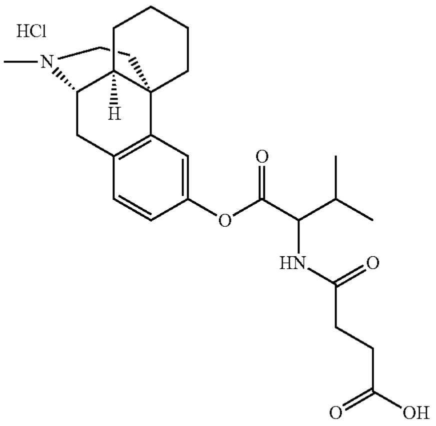

20 a HBTU, HOBt, TEA, DMF;
b 4N HCl/dioxane;
c 9, N-methylmorpholine, DMF;
d succinic anhydride, DMF

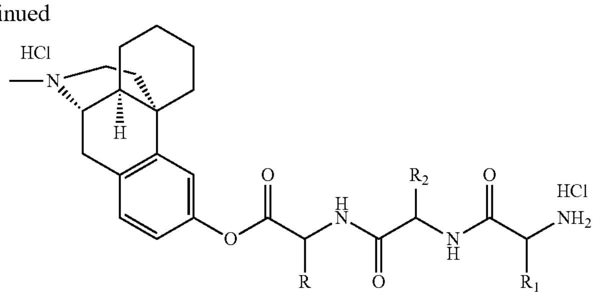

15: R = $(CH_3)_2CH$, $R_1 = R_2 = CH_3$
16: R = Ph—$CH_2$, $R_1 = R_2 = (CH_3)_2CH$
17: R = Ph—$CH_2$, $R_1 = R_2$ = Ph—$CH_2$
18: R = Ph—$CH_2$—, $R_1$ —CH—NH = $R_2$ —CH—NH = pyrrolidine
19: R = $CH_3$, $R_1 = R_2 = H$ 3-Val-dextrorphan 6

To a solution of dextrorphan, BocValOH and trimethylamine in DMF is added a solution of HBTU in DMF. The reaction mixture is stirred at room temperature overnight. The reaction is quenched with water and the solvent is evaporated under reduced pressure. The residue is taken in EtOAc, washed with 5% aq. $NaHCO_3$ and brine. The organic part is dried over anhydrous $Na_2SO_4$ and is evaporated to dryness to give 3-(Boc-Val)-dextrorphan 3.

A solution of 3-(Boc-Val)-dextrorphan 3 in 4N HCl in dioxane is stirred at room temperature. The solvent is evaporated under reduced pressure, the residue is co-evaporated with IPAc and dried to give compound 6.

3-Phe-dextrorphan 7

A solution of HBTU is added to a solution of dextrorphan, Boc-Phe-OH, HOBt and trimethylamine in DMF is added. The reaction mixture is stirred at room temperature. The reaction is quenched with water and the solvent is evaporated under reduced pressure. The residue is taken in EtOAc, and is finished with 5% aq. $NaHCO_3$ and brine. The organic part is dried over anhydrous $Na_2SO_4$ and is evaporated to dryness to give 3-(Boc-Phe)-dextrorphan 4.

A solution of 3-(Boc-Phe)-dextrorphan 4 in 4N HCl in dioxane is stirred at room temperature. The solvent is evaporated under reduced pressure, the residue is co-evaporated with IPAc and is dried to give the compound 7.

3-Ala-dextrorphan 8

Reaction of 1 and Boc-Ala-OH is performed following the same procedure as described for the synthesis of compound 7 to produce compound 5. Deprotection of 5 with 4N HCl in dioxane gives compound 8.

3-(AlaAlaVal)-dextrorphan 15

To a solution of 3-Val-dextrorphan 6 in DMF is added N-methylmorpholine and Boc-Ala-Ala-OSu. The reaction mixture is stirred at room temperature. The reaction is quenched with water and the solvent is evaporated under reduced pressure. The residue is partitioned between EtOAc and 5% aqueous $NaHCO_3$. The EtOAc layer is finished with 5% aq. $NaHCO_3$, brine, dried over anhydrous $Na_2SO_4$ and is evaporated to dryness to give 3-(Boc-AlaAlaVal)-dextrorphan 10.

The tripeptide derivative 10 is dissolved in 4N HCl in dioxane and is stirred at room temperature. Solvent is evaporated, the residue is co-evaporated with IPAc and is dried to give the tripeptide derivative 15.

3-(ValValPhe)-dextrorphan 16

To a solution of 3-Phe-dextrorphan 7 and N-methylmorpholine in DMF is added Boc-Val-Val-OSu. The reaction mixture is stirred at room temperature and is then heated. The reaction is quenched with water and the solvent is evaporated under reduced pressure and gives 3-(Boc-ValValPhe)-dextrorphan 11.

A solution of compound 11 in 4N HCl in dioxane is stirred at room temperature. Solvent is evaporated, the residue is co-evaporated with IPAc and is dried to give the tripeptide derivative 16.

3-(PhePhePhe)-dextrorphan 17

To a solution of 3-Phe-dextrorphan 7 in DMF is added N-methylmorpholine and Boc-PhePhe-OSu. The reaction mixture is stirred at room temperature. The reaction is quenched with water and the solvent is evaporated under reduced pressure. The residue is taken in EtOAc and is finished with 5% aqueous $NaHCO_3$, and brine. The organic part is dried over anhydrous $Na_2SO_4$ and is evaporated to dryness to give 3-(Boc-PhePhePhe)-dextrorphan 12.

Compound 12 is dissolved in 4N HCl in dioxane and is stirred at room temperature. Solvent is evaporated, the residue is co-evaporated with IPAc and is dried to give the tripeptide derivative 17.

3-(ProProPhe)-dextrorphan 18

Compound 18 is prepared following the procedure described for the synthesis of compound 16, except Boc-ProPro-OSu is used in place of Boc-ValVal-OSu.

3-(GlyGlyAla)-dextrorphan 19

A mixture of compound 8, N-methylmorpholine and Boc-GlyGly-OSu in DMF is stirred at room temperature. Solvent is evaporated under reduced pressure to give the tripeptide derivative 14.

A solution of 14 in 4N HCl in dioxane is stirred at room temperature. Solvent is removed under vacuum, the residue is co-evaporated with IPAc and is dried to give 19.

3-(N-succinoyl-Val)-dextrorphan 20

A solution of compound 6, triethylamine and succinic anhydride in DMF is heated. Solvent is evaporated under reduced pressure and provides 3-(N-succinoyl-Val)-dextrorphan. The purified product is treated with 4N HCl in dioxane to give the hydrochloride salt 20.

Scheme 2

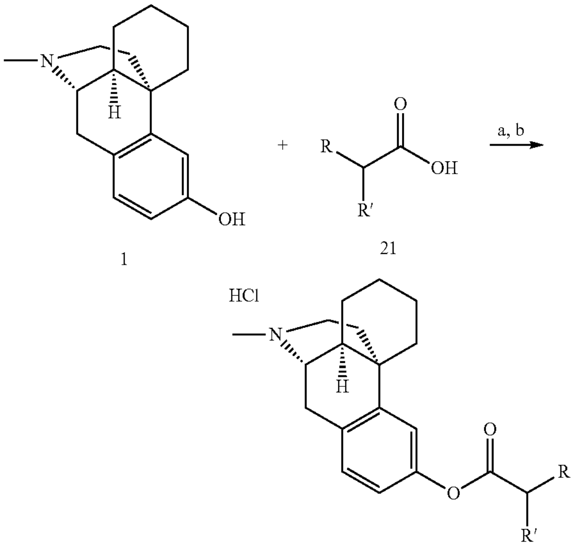

1

21

22: R = BzNH—, R′ = H

23: R = AcNH, R′ = $CH_3$—$CH_2$—$CH(CH_3)$

24: R = AcNH, R′ = 4-tert-butyloxybenzyl

25: R = AcNH, R′ = 4-hydroxybenzyl

26: R = OAc, R′ = Ph a 21, HBTU, HOBtM TEA, DMF;
b 4N HCl/dioxane

3-Hippuryl-dextrorphan 22

To a solution of dextrorphan 1, hippuric acid, HOBt and trimethylamine in DMF is added a solution of HBTU in DMF. The reaction mixture is stirred at room temperature. The reaction is quenched with water and the solvent is evaporated under reduced pressure. The residue is taken in EtOAc, and is finished with 5% aq. $NaHCO_3$ and brine. The EtOAc part is dried over anhydrous $Na_2SO_4$ and is evaporated to dryness to give 3-hippuryl-dextrorphan. The purified product is dissolved in 4N HCl in dioxane and is stirred at room temperature. The solvent is evaporated under reduced pressure, and the residue is co-evaporated with IPAc and is dried to obtain hydrochloride salt 22.

3-(N-acetyl-Ile)-dextrorphan 23

Reaction of dextrorphan with Ac-Ile-OH is carried out in a manner similar to that described for the synthesis of 22 to obtain 3-(N-acetyl-Ile)-dextrorphan. The N-acetyl-isoleucine derivative is converted to the corresponding hydrochloride salt by treatment with 4N HCl in dioxane to give the hydrochloride salt 23.

3-(N-acetyl-Tyr)-aextrorphan 25

Reaction of dextrorphan, Ac-Tyr($^t$Bu)-OH to give compound 24 is carried out following the same procedure as described for the synthesis of 22.

A solution of 24 in 4N HCl in dioxane is stirred at room temperature. Solvent is evaporated and the residue is co-evaporated with IPAc and is dried to give compound 25.

3-(Acetyl-OCH(phenyl)C(O))-dextrorphan 26

The reaction of dextrorphan and O-acetylmandelic acid is carried out following the same procedure as described for the synthesis of 22. The crude product is purified and is then converted to the HCl salt by treatment with 2N HCl in dioxane to produce hydrochloride salt 26.

Scheme 3

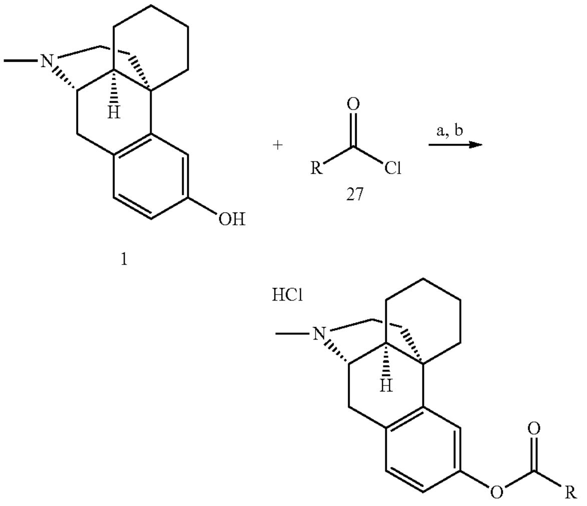

1

27

28: R = Ph—CH═CH—

29: R = AcO—$CH_2$—

30: R = $CH_3$—CH(OAc)— a 27, TEA, $CH_2Cl_2$;
b HCl/dioxane

3-Cinnamoyl-dextrorphan 28

A solution of cinnamoyl chloride in $CH_2Cl_2$ is added to a solution of dextrorphan 1 and trimethylamine in $CH_2Cl_2$. After the addition, the reaction mixture is stirred. Additional $CH_2Cl_2$ is added and the organic part is finished with 5% aqueous $NaHCO_3$, and brine. The $CH_2Cl_2$ part is dried over anhydrous $Na_2SO_4$ and is evaporated to dryness to afford 3-cinnamoyl-dextrorphan. The purified product is dissolved in 4N HCl in dioxane and is stirred at room temperature. Solvent is evaporated under vacuum and the residue is dried to give hydrochloride salt of 28.

3-(Acetyl-$OCH_2C(O)$)-dextrorphan 29

A solution of dextrorphan 1 and trimethylamine in $CH_2Cl_2$ is cooled and a solution of acetyloxyacetyl chloride in $CH_2Cl_2$ is added drop wise. After the addition, the reaction mixture is stirred at room temperature. The reaction is quenched with water and the solvent is evaporated under reduced pressure. The product is purified and is treated with 2N HCl in dioxane to give hydrochloride salt 29.

3-(Acetyl-OCH($CH_3$)C(O))-dextrorphan 30

A solution O-acetyl lactyl chloride in $CH_2Cl_2$ is added to a solution of dextrorphan 1 and trimethylamine in $CH_2Cl_2$. After the addition, the reaction mixture is stirred. Solvent is evaporated under reduced pressure. The residue is dissolved in $CH_2Cl_2$ and is finished with 5% aqueous $NaHCO_3$ and brine. The $CH_2Cl_2$ part is dried over anhydrous $Na_2SO_4$ and is evaporated to dryness. The crude product is purified and is converted to the corresponding hydrochloride salt 30 by treatment with 2N HCl in dioxane.

3-(Chloromethyloxycarbonyl)-dextrorphan 32

A solution of chloromethyl chloroformate 31 in $CH_2Cl_2$ is added to a solution of dextrorphan and trimethylamine in $CH_2Cl_2$. After the addition, the reaction mixture is stirred. The reaction is quenched with water and solvent is evaporated under reduced pressure. The residue is taken in EtOAc, and is finished with water and brine, is dried over anhydrous $Na_2SO_4$ and is evaporated to dryness to give 32.

3-(Benzoyl-$OCH_2OC$(O)-dextrorphan 34

A solution of 32 and sodium benzoate in DMF is heated. Solvent is evaporated under reduced pressure. The residue is taken in EtOAc, and is finished with 5% aq. $NaHCO_3$ and brine. The organic part is dried over anhydrous $Na_2SO_4$ and is evaporated to dryness to give 34. The purified benzoyl Scheme 4

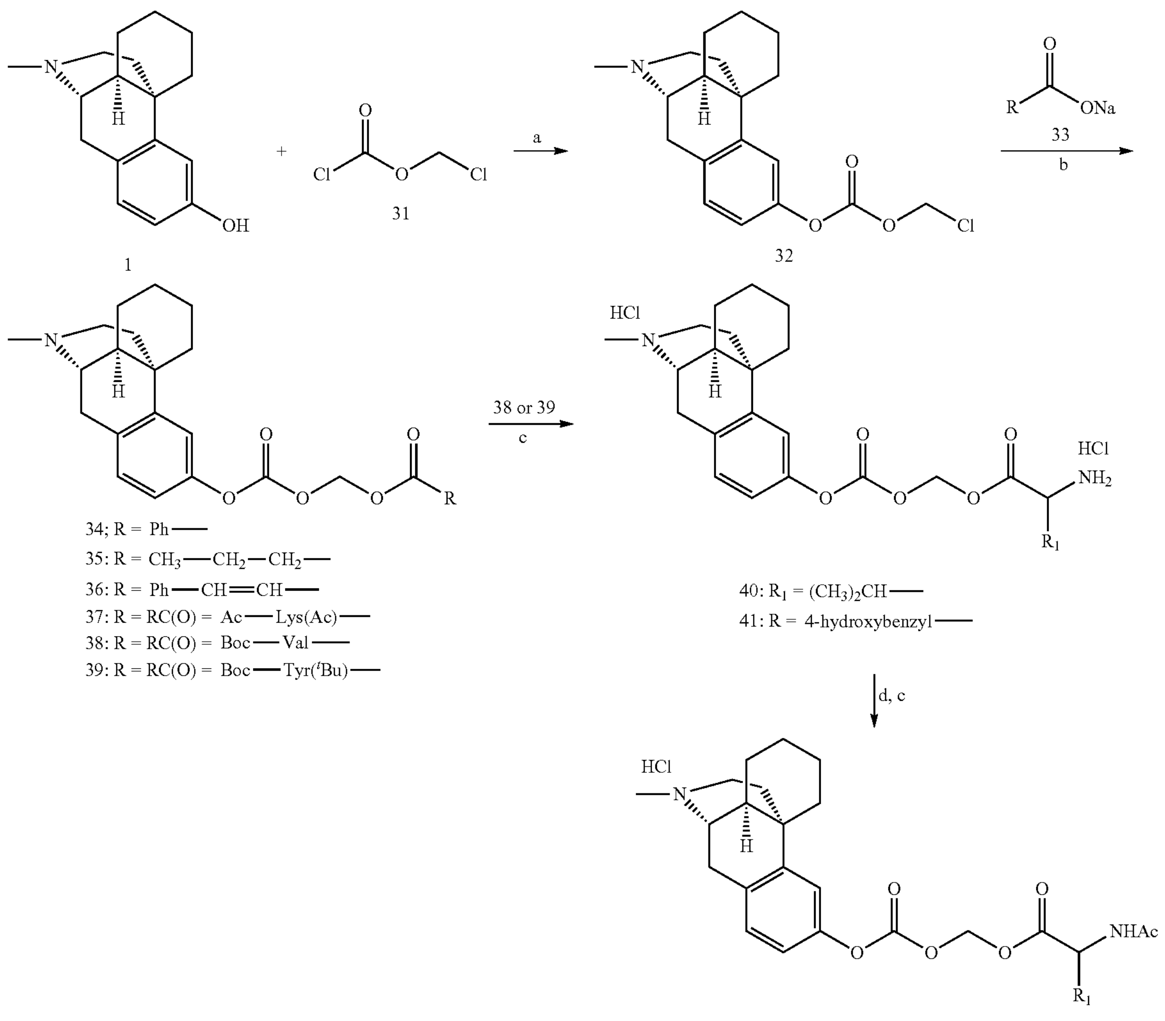

1

31

32

34; R = Ph—

35: R = $CH_3$—$CH_2$—$CH_2$—

36: R = Ph—CH=CH—

37: R = RC(O) = Ac—Lys(Ac)—

38: R = RC(O) = Boc—Val—

39: R = RC(O) = Boc—Tyr($^t$Bu)—

40: $R_1$ = $(CH_3)_2CH$—

41: R = 4-hydroxybenzyl—

42: $R_1$ = $(CH_3)_2CH$—

43: R = 4-hydroxybenzyl— a TEAM $CH_2Cl_2$;
b 33, DMF, heat;
c 4N HCl/dioxane;
d Acetyl chloride, TEA, $CH_2Cl_2$;
e HCl/dioxane derivative is dissolved in 4N HCl in dioxane, is stirred at room temperature, and then solvent is evaporated under vacuum. The resulting residue is dried to give the hydrochloride salt of 34.

3-(Butanoyl-OCH2OC(O))-dextrorphan 35

Reaction of 32 with sodium butyrate to obtain 35 is carried out in a manner similar to that described for the synthesis of 34. The crude product is purified and is treated with 4N HCl in dioxane to obtain hydrochloride salt of 35.

3-(Cinnamoyl-$OCH_2OC(O)$)-dextrorphan 36

A solution of 32 and sodium cinnamate in DMF is heated. Solvent is evaporated under reduced pressure. The residue is taken in EtOAc, and is finished with 5% aq. $NaHCO_3$ and brine. The organic part is dried over anhydrous $Na_2SO_4$ and is evaporated to dryness. The crude product is isolated as hydrochloride salt of 36 by treatment with 4N HCl in dioxane.

3-(N,O-Acetyl-Lys-$OCH_2OC(O)$)-dextrorphan 37

A solution of 32 and Ac-Lys(Ac)-ONa in DMF is heated. Solvent is evaporated under reduced pressure. The residue is taken in EtOAc, and is finished with 5% aq. $NaHCO_3$ and brine. The organic part is dried over anhydrous $Na_2SO_4$ and is evaporated to dryness. The crude product is purified and is treated with 4N HCl in dioxane to give hydrochloride salt of 37.

General Procedure for the Synthesis of Sodium Salt of N-Protected Amino Acids (Boc-AA-ONa):

To a solution or suspension or solution (depending on amino acids) of Boc-AA-OH in $CH_3CN$/water is added 1N NaOH drop wise while stirring.

3-(Boc-Val-$OCH_2OC(O)$)-dextrorphan 38

A solution of 32 and Boc-Val-ONa in DMF is heated. Solvent is evaporated under reduced pressure. The residue is taken in EtOAc, and is finished with 5% aq. $NaHCO_3$ and brine. The organic part is dried over anhydrous $Na_2SO_4$ and is evaporated to dryness to give 38.

3-(Val-$OCH_2OC(O)$)-dextrorphan 40

A solution of 38 in 4N HCl in dioxane is stirred at room temperature. Solvent is evaporated under reduced pressure, the residue is co-evaporated with IPAc and is dried to give 40. Compound 40 is converted to the acetyl derivative 42.

3-(N-Acetyl-Val-$OCH_2OC(O)$)-dextrorphan 42

A solution of 40 and TEA in $CH_2Cl_2$ is cooled and a solution of acetyl chloride in $CH_2Cl_2$ is added drop wise. The reaction mixture is stirred at room temperature. Solvent is evaporated under reduced pressure and the residue is partitioned between EtOAc and 5% aqueous $NaHCO_3$. The EtOAc layer is finished with 5% aq. $NaHCO_3$ and brine, is dried over anhydrous $Na_2SO_4$ and is evaporated to dryness.

The purified product is dissolved in 4N HCl in dioxane, is stirred and is then evaporated to dryness under vacuum to give the hydrochloride salt 42.

3-(N,O-diacetyl-Tyr)-dextrorphan 43

A solution of 32 and Boc-Tyr($^t$Bu)-ONa in DMF is stirred at room temperature, and then is heated. Solvent is evaporated under reduced pressure. The residue is dissolved in EtOAc, and is finished with 5% aq. $NaHCO_3$ and brine. The organic part is dried over anhydrous $Na_2SO_4$ and is evaporated to dryness to give 39.

Compound 39 is dissolved in 4N HCl in dioxane and the solution is stirred at room temperature. Solvent is evaporated under reduced pressure, and the residue is co-evaporated with IPAc and is dried to give 41.

A solution of 41 and TEA in $CH_2Cl_2$ is cooled and a solution of acetyl chloride in $CH_2Cl_2$ is added drop wise. After the addition, the reaction mixture is stirred at room temperature. Solvent is evaporated under reduced pressure and the residue is partitioned between EtOAc and 5% aqueous $NaHCO_3$. The EtOAc layer is finished with 5% aq. $NaHCO_3$ and brine, is dried over anhydrous $Na_2SO_4$ and is evaporated to dryness. The crude product is purified and is then treated with 4N HCl in dioxane to give the hydrochloride salt 43.

3-Biotinyl-dextrorphan 45

Scheme 5

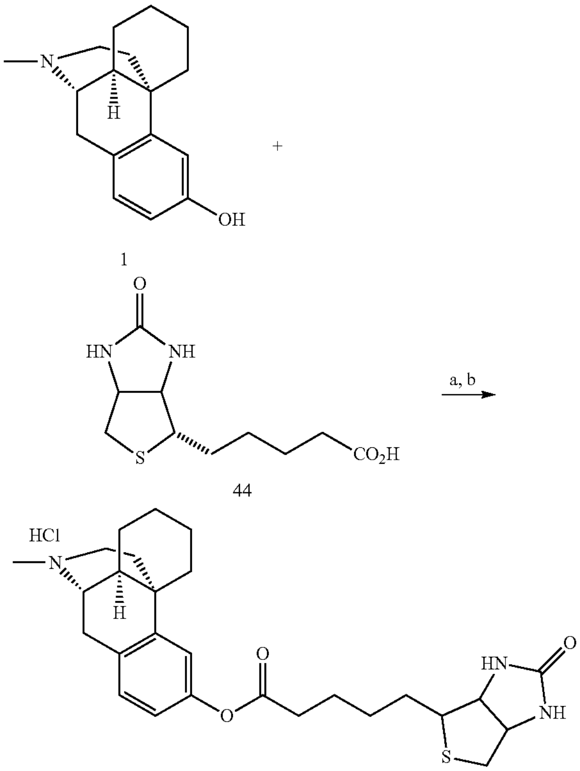

1 + 44 → 45

(a) HBTU, HOBt, TEA, DMF;
(b) HCl/dioxane

A solution of HBTU in DMF is added to a solution of dextrorphan 1, biotin 44, HOBt and trimethylamine in DMF at room temperature. The reaction is quenched with water and the solvent is evaporated under reduced pressure. 5% Aqueous $NaHCO_3$ is added to the residue and the mixture is extracted with $CH_2Cl_2$. The combined organic parts is finished with 5% aq. $NaHCO_3$ and brine, is dried over anhydrous $Na_2SO_4$ and is evaporated to dryness to give 3-biotinyl-dextrorphan. The crude product is purified and is treated with 4N HCl in dioxane to give the hydrochloride salt 45.

Scheme 6

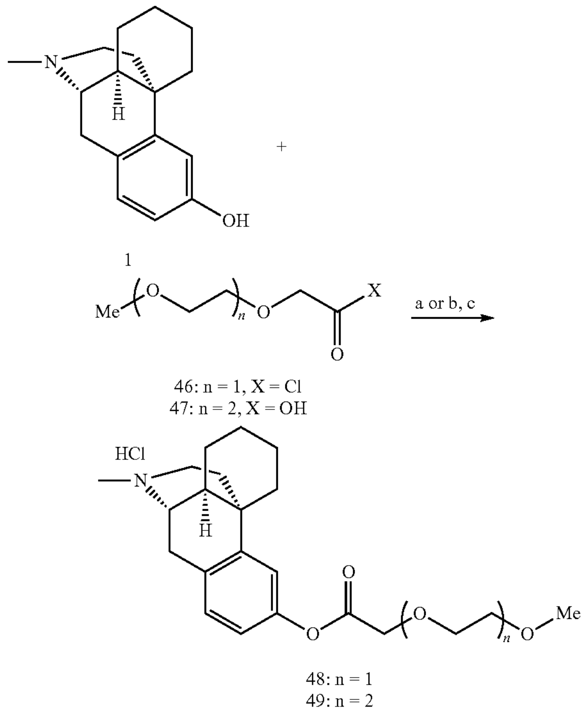

1

46: n = 1, X = Cl
47: n = 2, X = OH

48: n = 1
49: n = 2

(a) 46, TEA, $CH_2Cl_2$;
(b) 47, HBTU, HOBt, TEA, DMF;
(c) HCl/dioxane 3-(Methoxy-(ethoxy)-$CH_2C(O)$)-dextrorphan 48

A solution of 2-methoxyethoxy acetyl chloride 46 in $CH_2Cl_2$ is added to a solution of dextrorphan and trimethylamine in $CH_2Cl_2$. After the addition, the reaction mixture is stirred. Additional $CH_2Cl_2$ is added, and the organic part is finished with 5% aqueous $NaHCO_3$ and brine. The $CH_2Cl_2$ part is dried over anhydrous $Na_2SO_4$ and is evaporated to dryness. The residue is purified, is dissolved in 4N HCl in dioxane, is stirred at room temperature, and is then evaporated under reduced pressure to give the hydrochloride salt 48.

3-(Methoxy-$PEG_2$-$CH_2C(O)$)-dextrorphan 49

To a solution of dextrorphan 1, 2-[2-(2-Methoxyethoxy) ethoxy] acetic acid 47, HOBt and trimethylamine in DMF is added a solution of HBTU in DMF. The reaction mixture is stirred at room temperature. The reaction is quenched with water and the solvent is evaporated under reduced pressure. The residue is partitioned between $CH_2Cl_2$ and 5% aq. $NaHCO_3$. The aqueous part is extracted with $CH_2Cl_2$. The combined organic part is finished with brine, is dried over anhydrous $Na_2SO_4$ and is evaporated to dryness. The purified product is dissolved in 2N HCl in dioxane, is stirred at room temperature and is then evaporated under reduced pressure to give the hydrochloride salt 49.

Scheme 7

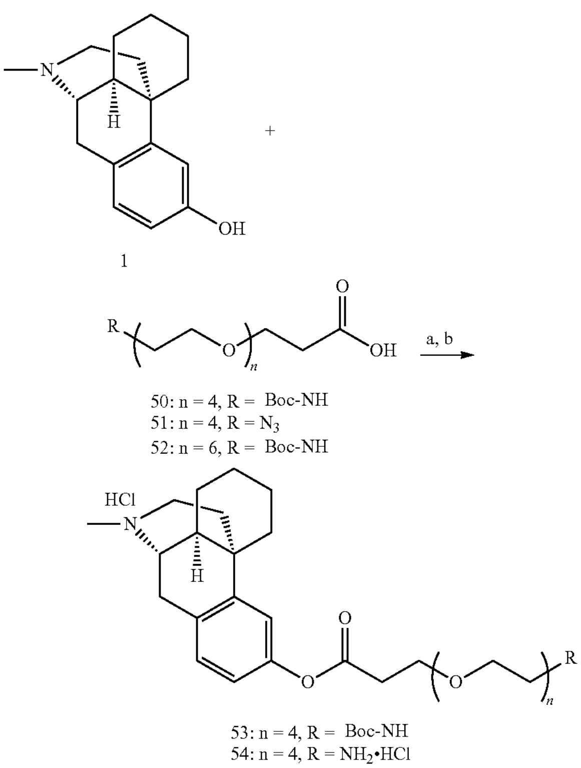

1

50: n = 4, R = Boc-NH
51: n = 4, R = $N_3$
52: n = 6, R = Boc-NH

53: n = 4, R = Boc-NH
54: n = 4, R = $NH_2$•HCl
55: n = 4, R = $N_3$
56: n = 6, R = Boc-NH
57: n = 6, R = $NH_2$•HCl (a) HBTU, HOBt, TEA, DMF;
(b) 4N HCl/dioxane 3-($H_2N$-$PEG_4$-$CH_2CH_2C(O)$)-dextrorphan 54

To a solution of dextrorphan 1, Boc-NH-$(PEG)_4$-$CH_2CH_2$—COOH 50, HOBt and trimethylamine in DMF is added a solution of HBTU in DMF. The reaction mixture is stirred at room temperature. The reaction is quenched with water and the solvent is evaporated under reduced pressure. The residue is taken in EtOAc, is finished with 5% aq. $NaHCO_3$ and brine. The organic part is dried over anhydrous $Na_2SO_4$ and is evaporated to dryness to give 53.

A solution of 53 in 4N HCl in dioxane is stirred at room temperature. Solvent is evaporated under pressure, the residue is co-evaporated with IPAc and is dried to give the deprotected product 43.

3-($N_3$-$PEG_4$-$CH_2CH_2C(O)$)-dextrorphan 55

A solution of HBTU in DMF is added to a solution of dextrorphan 1, $N_3$-$(PEG)_4$-$CH_2CH_2$—COOH 51, HOBt and trimethylamine in DMF. The reaction mixture is stirred at room temperature. The reaction is quenched with water and the solvent is evaporated under reduced pressure. The residue is taken in $CH_2Cl_2$, is finished with 5% aq. $NaHCO_3$ and brine. The organic part is dried over anhydrous $Na_2SO_4$ and is evaporated to dryness. The purified product is dissolved in 2N HCl in dioxane and is stirred at room temperature. Solvent is evaporated under pressure, is co-evaporated with IPAc and is dried to give the hydrochloride salt 55.

3-($H_2N$-$PEG_6$-$CH_2CH_2C(O)$)-dextrorphan 57

To a solution of dextrorphan 1, Boc-NH-$(PEG)_6$-$CH_2CH_2$—COOH, HOBt and trimethylamine in DMF is added a solution of HBTU in DMF. The reaction mixture is stirred at room temperature. The reaction is quenched with water and the solvent is evaporated under reduced pressure. The residue is taken in $CH_2Cl_2$, and is finished with 5% aq. $NaHCO_3$ and brine. The organic part is dried over anhydrous $Na_2SO_4$ and is evaporated to dryness to give 56.

A solution of 56 in 4N HCl in dioxane is stirred at room temperature. Solvent is evaporated under pressure, the residue is co-evaporated with IPAc, and is dried to give the deprotected product 57.

Scheme 8

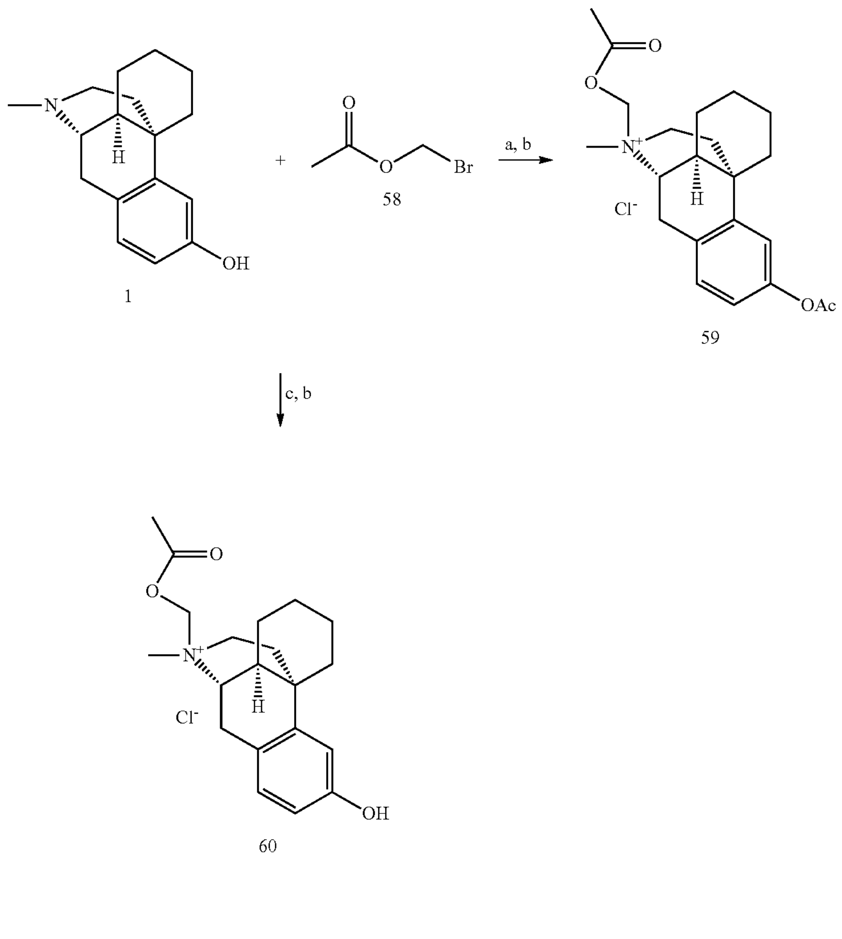

1 58 59 60

(a) 1,2,2,6,6-Pentamethylpiperidine $CH_3CH$, heat;
(b) 4N HCl/dioxane;
(c) $CH_3CN$, heat.

3-Acetyl-N-(acetyl-$OCH_2$)-dextrorphanium 3

A solution of dextrorphan 1,1,2,2,6,6-pentamethylpiperidine and acetyloxymethyl bromide 58 in $CH_3CN$ is heated. Solvent is evaporated under reduced pressure. The purified quaternary salt is dissolved in 4N HCl in dioxane and is stirred at room temperature. The solvent is evaporated, the residue is co-evaporated with IPAc and is dried to give the chloride salt 59.

N-(Acetyl-$OCH_2$)-dextrorphanium 60

A solution of dextrorphan 1 and acetyloxymethyl bromide 58 in $CH_3CN$ is heated. Solvent is evaporated under reduced pressure. The purified quaternary salt is dissolved in 4N HCl in dioxane and is stirred at room temperature. The solvent is evaporated, the residue is co-evaporated with IPAc and is dried to give the chloride salt 60.

Scheme 9

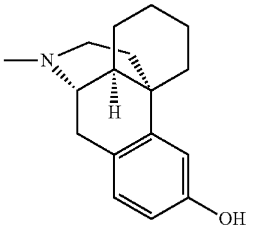

1

+

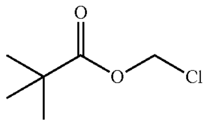

61

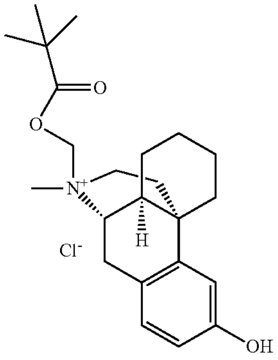

62

+

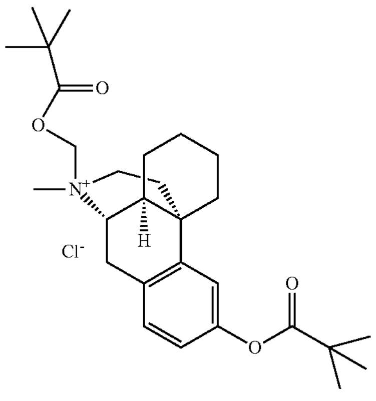

63

+

-continued

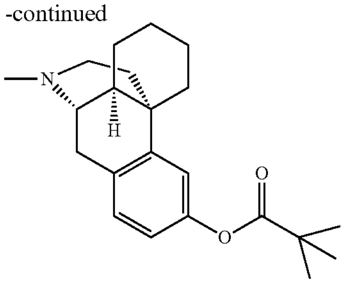

64

(a) $CH_3CH$, heat;
(b) Dowex 1 × 4 chloride, water/$CH_3CH$;
(c) 1,2,2,6,6-Pentamethylpiperidine $CH_3CH$, heat.

N-(Pivaloyl-$OCH_2$)-dextrorphanium 62, 3-pivaloyl-N-(pivaloyl-$OCH_2$)-dextrorphanium chloride 63 and 3-pivaloyl-dextrorphan 64

A suspension of dextrorphan 1 and chloromethyl pivalate 61 in $CH_3CN$ is heated. Solvent is evaporated under reduced pressure. The quaternary salts, after separation, is treated with Dowex 1x4 chloride form, is filtered and the filtrate is lyophilized to afford compound 62 and 63. In addition, conjugate 64 may form.

Prophetic Synthesis of Cbz-Val-O—$CH_2$—Cl

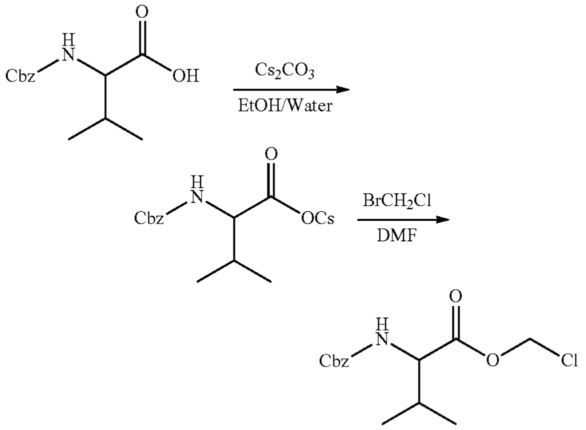

Prophetic Synthesis of N-(Val-$CH_2$)-dextrorphanium

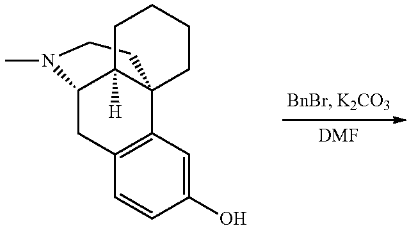

-continued
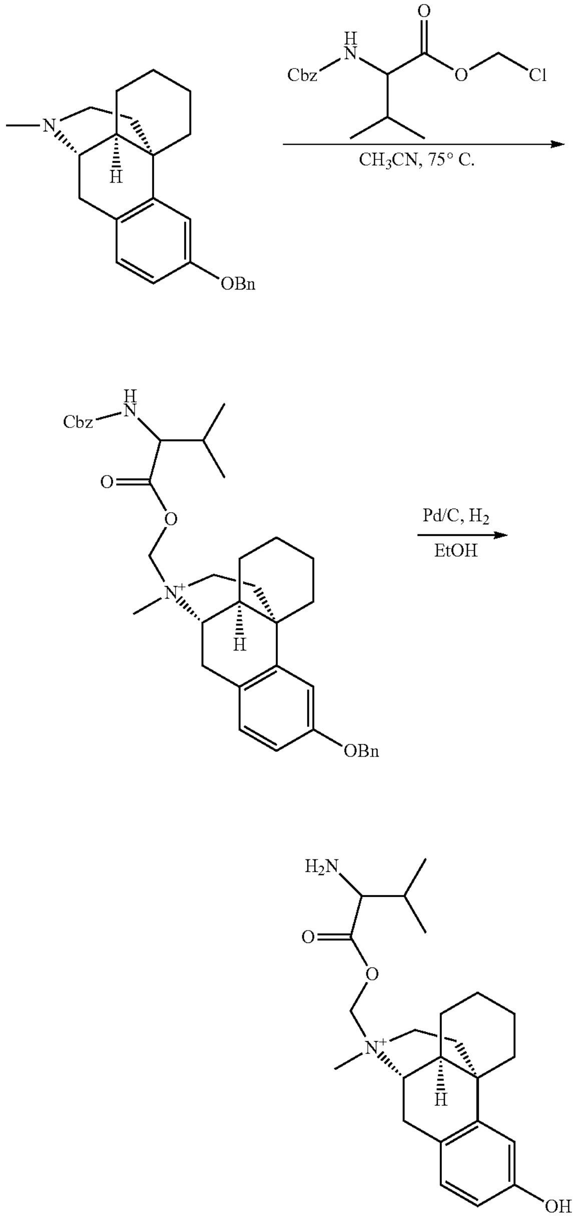
Prophetic Synthesis of MeO-PEG$_3$-CH$_2$C(O)OCH$_2$—Cl
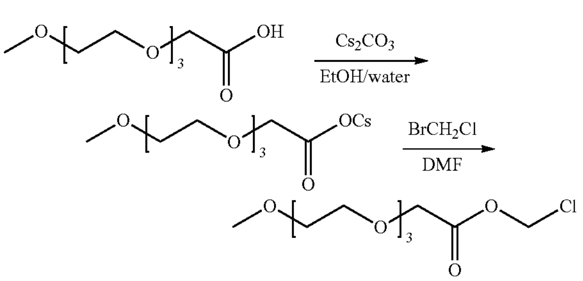
Prophetic Synthesis of N-(MeO-PEG$_3$-CH$_2$C(O)OCH$_2$)-dextrorphanium
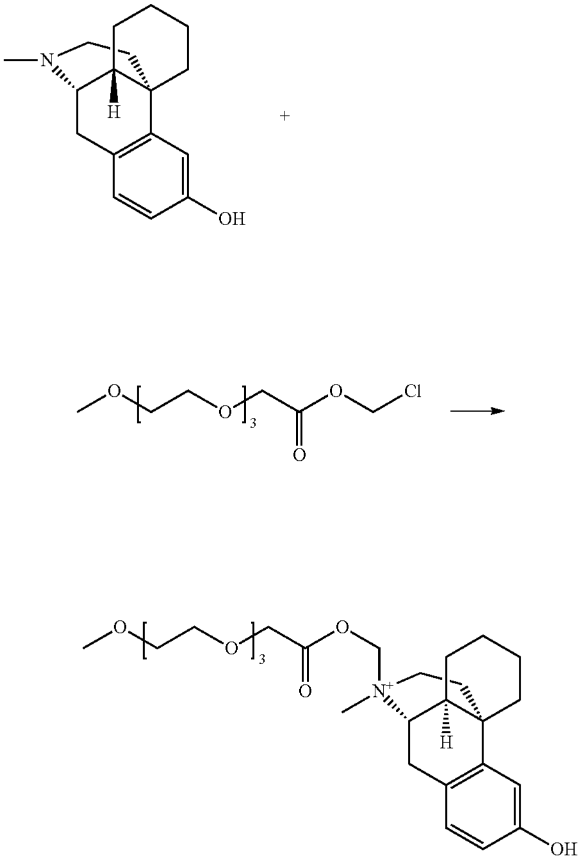
Prophetic Synthesis of Boc-Ser[C(O)—O—CH$_2$—Cl]-O$^t$Bu
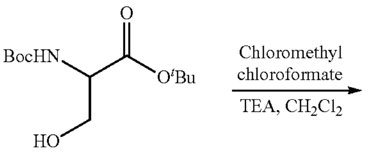
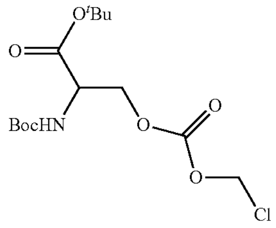

Prophetic Synthesis of N-[Ser{C(O)—O—$CH_2$}—OH]-dextrorphanium
Scheme 10
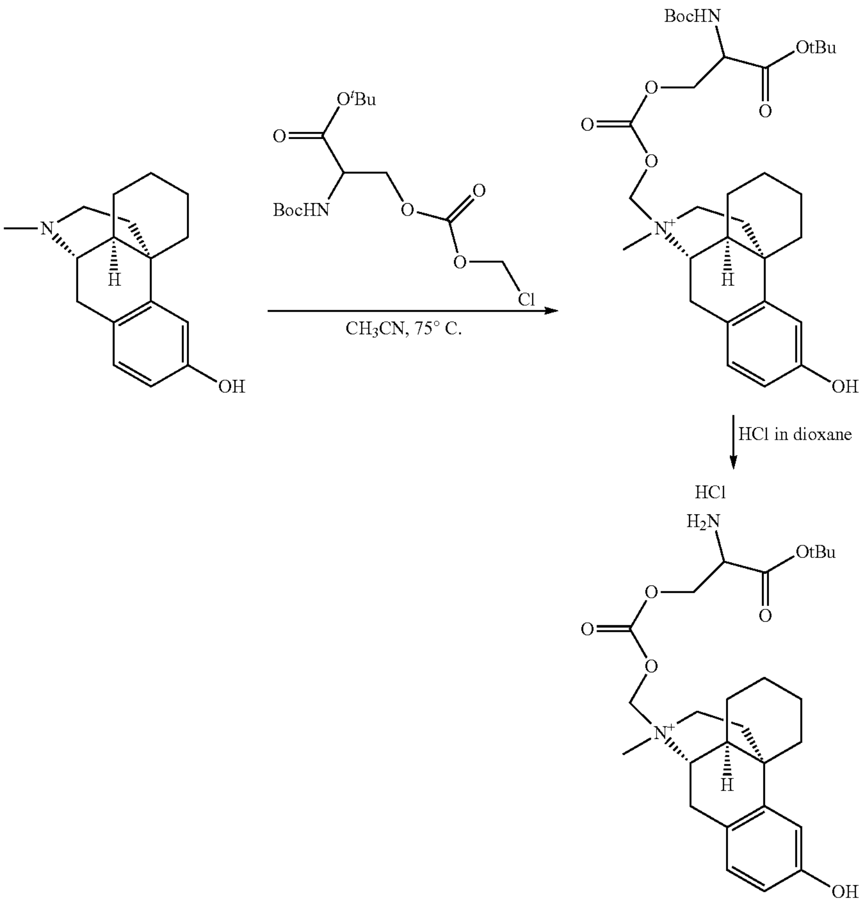
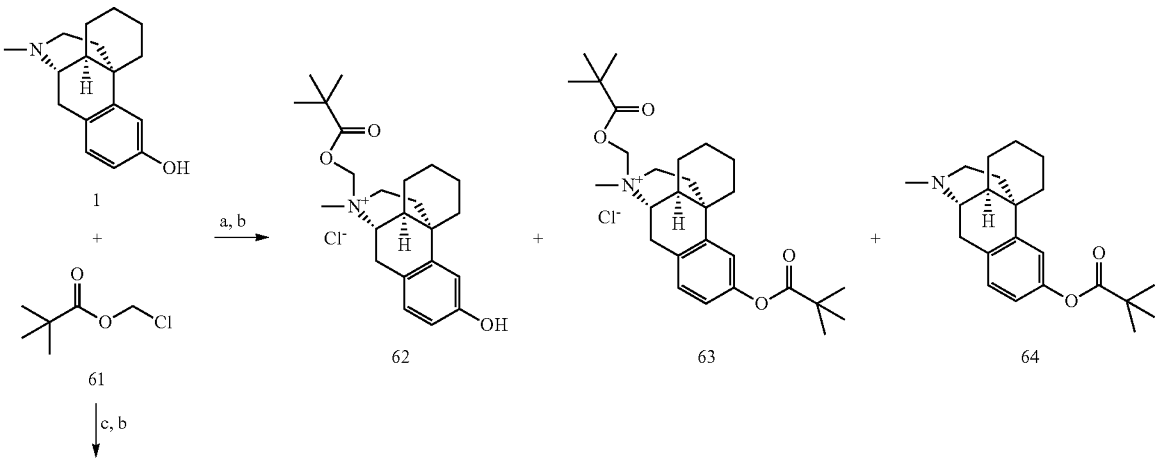

-continued

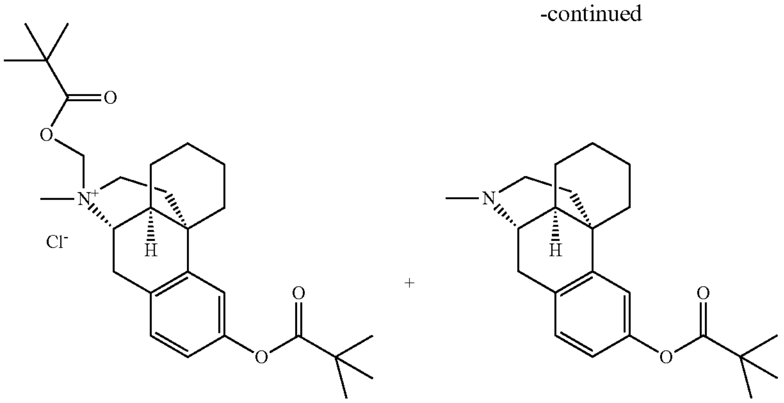

63 64

(a) $CH_3CN$, heat; (b) Dowex 1x4 chloride, water/$CH_3CN$; (c) 1,2,2,6,6-Pentamethylpiperidine $CH_3CN$, heat.

N-(pivaloyl-$OCH_2$)-dextrorphanium chloride 62, 3-pivaloyl-N-(pivaloyl-$OCH_2$)-dextrorphanium chloride 63 and 3-pivaloyl-dextrorphan 64

A suspension of dextrorphan 1 and chloromethyl pivalate 61 in $CH_3CN$ is heated. Solvent is evaporated under reduced pressure. The quaternary salts, after separation, is treated with Dowex 1×4 chloride form, is filtered and the filtrate is lyophilized to afford compound 62 and 63. In addition, 3-monosubstituted dextrorphan conjugate 64 may form.

3-pivaloyl-N-(pivaloyl-$OCH_2$)-dextrorphanium chloride 63 and 3-pivaloyl-dextrorphan 64

In an alternative reaction scheme, a mixture of dextrorphan 1,1,2,2,6,6-pentamethyl piperidine and chloromethyl pivalate 61 in $CH_3CN$ is heated. Solvent is evaporated under reduced pressure. The quaternary salt is treated with Dowex 1×4 chloride form and is lyophilized to give compound 63. In addition, 3-monosubstituted dextrorphan conjugate 64 may form.

Scheme 11

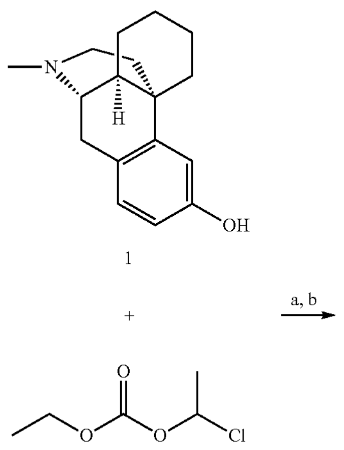

1

+

65

-continued

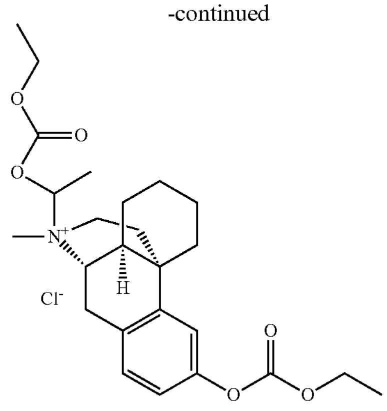

+

66

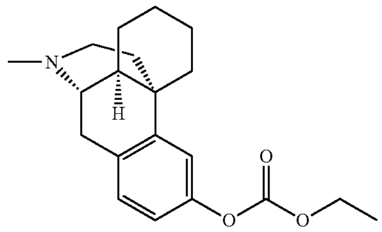

67

(a) 1,2,2,6,6-Pentamethylpiperidine $CH_3CN$, heat;
(b) Dowex 1 × 4 chloride, water/$CH_3CN$

3-(Ethoxy-C(O))—N-(ethoxy-C(O)CH($CH_3$))-dextrorphanium chloride 66 and 3-(ethoxy-C(O))-dextrorphan 67

A mixture of dextrorphan 1, 1-chloroethyl ethyl carbonate 65, 1,2,2,6,6-pentamethylpiperidine and NaI in $CH_3CN$ is heated. Solvent is evaporated under reduced pressure. The quaternary salt is treated with Dowex 1×4 chloride form, is filtered and the filtrate is lyophilized to give compound 66. In addition, 3-monosubstituted dextrorphan conjugate 67 may form.

Prophetic Synthesis of Boc-Phe-CH(Me)-COOH
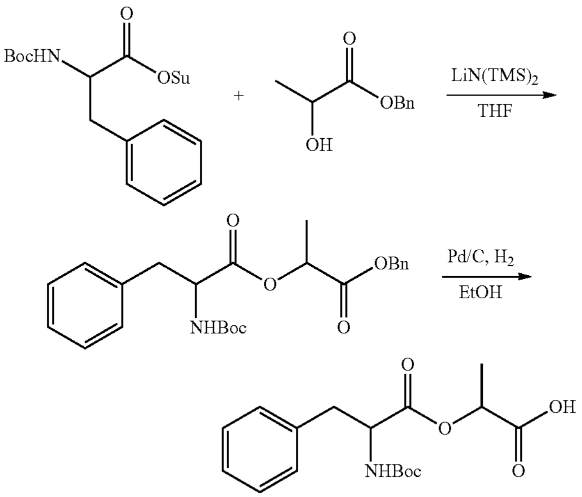
Prophetic Synthesis of nicotinoyl-O—$CH_2$—Cl
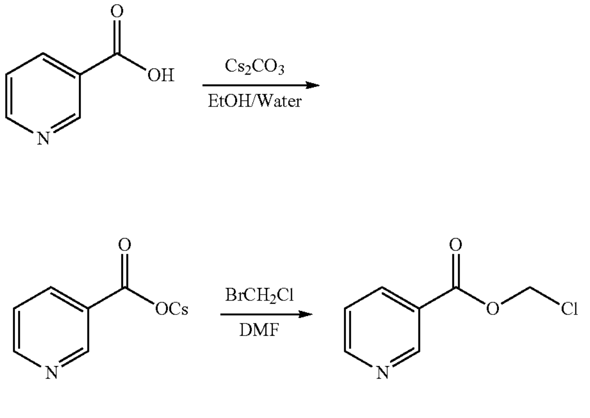
Prophetic Synthesis of 3-(Phe-CH(Me)C(O))—N-(nicotinoyl-$OCH_2$)-dextrorphanium
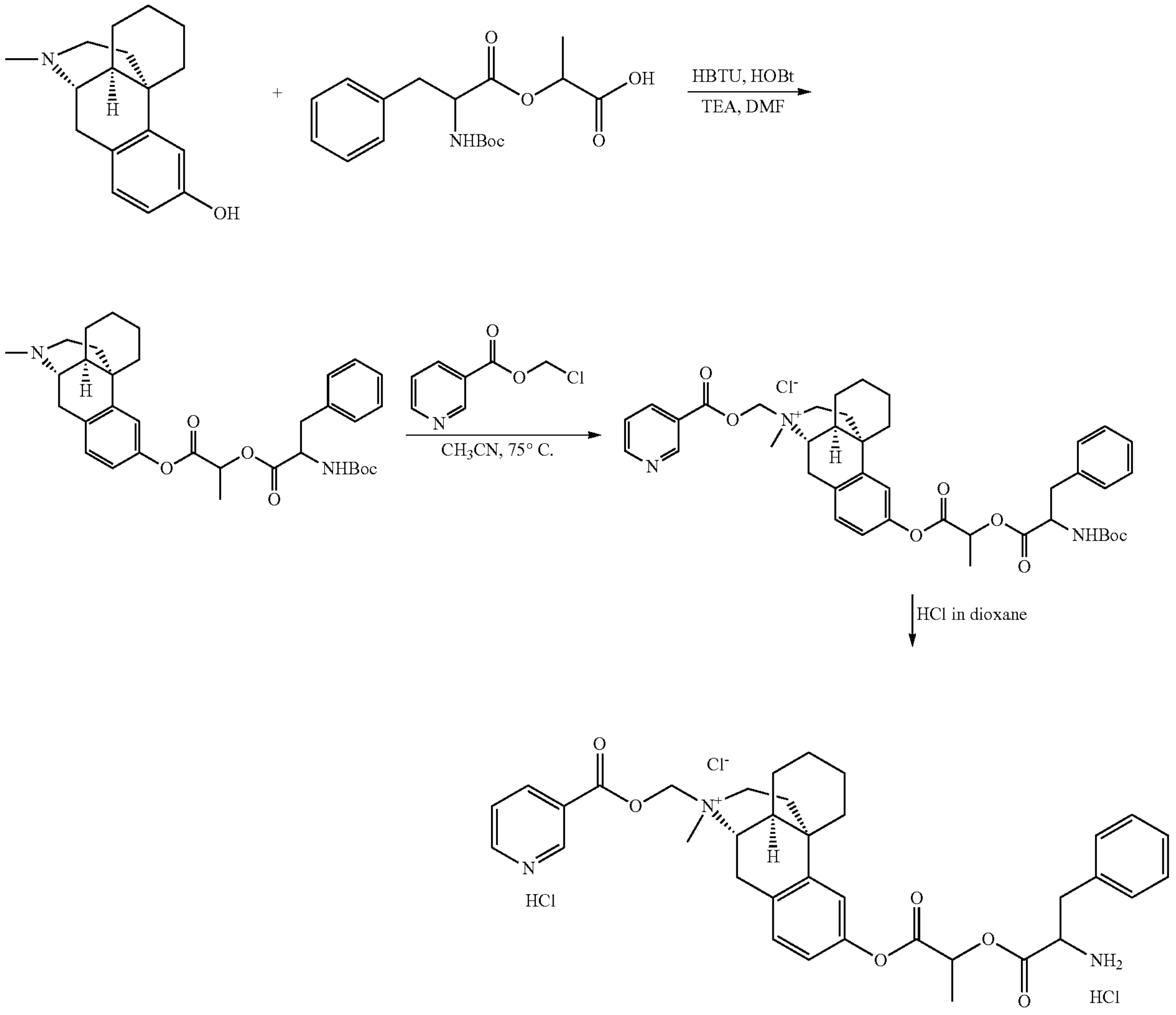

What is claimed is:

1. A compound having the following general formula:

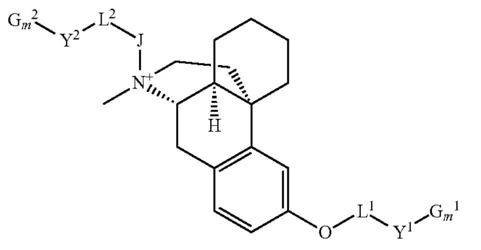

where $L^1$ is

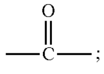

and $L^2$ is absent, or

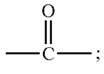

$Y^1$ and $Y^2$ are independently either absent, or $[A\text{-}X—Z]_n$ where A and Z are independently selected for $Y^1$ and $Y^2$, and are, independent of each other, either absent or selected from —O—, —S—, or $—(CR^1R^2)_k—$, and where X is $—(CR^1R^2)—$;

J is $[M\text{-}W]_p$ where M is $—(CR^3R^4)_q—$; and W is absent, or —O— or —S—

$R^1$ and $R^2$ are each independently selected for $Y^1$ and $Y^2$, and are, independent of each other, selected from H, alkyl, aryl, alkylaryl, alkoxy, haloalkyl, or haloaryl $R^3$ and $R^4$ are each independently selected from H, alkyl, aryl, alkylaryl, alkoxy, haloalkyl, or haloaryl for each $Y^1$ and $Y^2$, n is independently an integer of 1-4 for each repeating unit of $[A\text{-}X—Z]_n$, when $—(CR^1R^2)_k—$ is present, k is independently an integer of 1-4, p and q are independently selected from 1-4

$G^1_m$ and $G^2_m$ are independently absent, or selected independently of each other and, when present, each repeating subunit is independently selected from H, oxoacid, polyethylene glycol having from 2 to 5 ethylene oxide units, or a vitamin compound;

where m is selected independently for $G^1$ and $G^2$, and is an integer of 1-4, except that m is 1 when $G^1$ or $G^2$ is a hydrogen atom;

or a pharmaceutically acceptable salt thereof.

2. The compound of claim 1, wherein at least one of $G^1$ and $G^2$ is at least one oxoacid.

3. The compound of claim 2, wherein $G^1$ and $G^2$ are each acetic acid.

4. The compound of claim 1, wherein the compound is 3-acetyl-N-(acetyl-$OCH_2$)-dextrorphanium having the following structural formula:

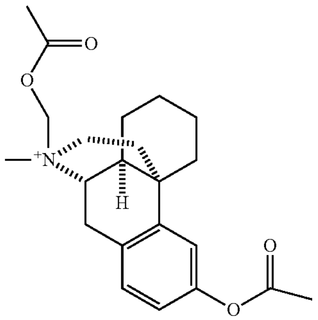

or a pharmaceutically acceptable salt thereof.

5. A composition wherein the composition comprises the compound of claim 1 or a pharmaceutically acceptable salt of the compound.

6. A composition wherein the composition comprises the compound of claim 4 or a pharmaceutically acceptable salt of the compound.

7. The composition of claim 5, wherein the pharmaceutically acceptable salt is selected from the group consisting of acetate, l-aspartate, besylate, bicarbonate, carbonate, d-camsylate, l-camsylate, citrate, edisylate, formate, fumarate, gluconate, hydrobromide/bromide, hydrochloride/chloride, d-lactate, i-lactate, d,l-lactate, d,l-malate, l-malate, mesylate, pamoate, phosphate, succinate, sulfate, bisulfate, d-tartrate, l-tartrate, d,l-tartrate, meso-tartrate, benzoate, gluceptate, d-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate (mucate), galacturonate, gallate, gentisate, glutamate, glutarate, glycerophosphate, heptanoate (enanthate), hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, or combinations thereof.

8. The composition of claim 6, wherein the pharmaceutically acceptable salt is selected from the group consisting of acetate, l-aspartate, besylate, bicarbonate, carbonate, d-camsylate, l-camsylate, citrate, edisylate, formate, fumarate, gluconate, hydrobromide/bromide, hydrochloride/chloride, d-lactate, i-lactate, d,l-lactate, d,l-malate, l-malate, mesylate, pamoate, phosphate, succinate, sulfate, bisulfate, d-tartrate, l-tartrate, d,l-tartrate, meso-tartrate, benzoate, gluceptate, d-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate (mucate), galacturonate, gallate, gentisate, glutamate, glutarate, glycerophosphate, heptanoate (enanthate), hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, or combinations thereof.

9. The composition of claim 5, wherein the compound is present in an amount of about 0.5 mg or higher.

10. The composition of claim 6, wherein the compound is present in an amount of about 0.5 mg or higher.

11. The composition of claim 5, wherein the compound is provided in a dosage form selected from the group consisting of a tablet, a capsule, a caplet, a suppository, a troche, a lozenge, an oral powder, a solution, a syrup, an oral film, a thin strip, a slurry, and a suspension.

12. The composition of claim 6, wherein the compound is provided in a dosage form selected from the group consisting of a tablet, a capsule, a caplet, a suppository, a troche, a lozenge, an oral powder, a solution, a syrup, an oral film, a thin strip, a slurry, and a suspension.

13. The composition of claim 5, wherein the composition comprises at least one additional active substance.

14. The composition of claim 13, wherein the at least one additional active substance is selected from the group consisting of a different dextrorphan conjugate or unconjugated dextrorphan.

15. The composition of claim 14, wherein the at least one additional active substance is a different dextrorphan conjugate.

16. The composition of claim 14, wherein the at least one additional active substance is unconjugated dextrorphan.

* * * * *